United States Patent [19]

Kleinberg et al.

[11] Patent Number: 5,055,787
[45] Date of Patent: Oct. 8, 1991

[54] BOREHOLE MEASUREMENT OF NMR CHARACTERISTICS OF EARTH FORMATIONS

[75] Inventors: Robert L. Kleinberg, Ridgefield; Douglas D. Griffin, Bethel; Masafumi Fukuhara; Abdurrahman Sezginer, both of Ridgefield, all of Conn.; Weng C. Chew, Champaign, Ill.

[73] Assignee: Schlumberger Technology Corporation, New York, N.Y.

[21] Appl. No.: 431,368

[22] Filed: Dec. 5, 1989

Related U.S. Application Data

[60] Division of Ser. No. 368,916, Jun. 19, 1989, Pat. No. 4,933,638, which is a continuation of Ser. No. 901,084, Aug. 27, 1986, abandoned.

[51] Int. Cl.$^5$ .............................................. G01R 33/20
[52] U.S. Cl. .................................................... 324/303
[58] Field of Search ............... 324/300, 303, 307, 309, 324/310, 311, 312, 313, 314, 318, 322

[56] References Cited

U.S. PATENT DOCUMENTS 3,042,855  7/1962  Brown .
3,083,335  3/1963  Schuster .
3,289,072  11/1966  Schuster .

(List continued on next page.)

FOREIGN PATENT DOCUMENTS 2141236A  12/1984  United Kingdom .

OTHER PUBLICATIONS

Herrick, Couturie & Best, "An Improved Nuclear Magnetism Logging System and Its Application to Formation Evaluation", 54th *Annual Fall Technical Conference and Exhibition of the Soc. of Petroleum Engineers* (A.I.M.E., Dallas, Tex., Las Vegas, Nev., Sep. 23–26, 1979.

(List continued on next page.)

Primary Examiner—Michael J. Tokar
Attorney, Agent, or Firm—Martin M. Novack; Leonard W. Pojunas

[57] ABSTRACT

Borehole NMR logging apparatus and methods, and methods for the interpretation thereof. A logging tool is provided which produces a strong, static and homogeneous magnetic field $B_0$ in a Volume of an adjacent formation on one side of the tool to measure nuclear magnetic resonance characteristics thereof. In the preferred embodiment, the tool has an RF antenna mounted on the outside of the metal body of the tool, directing focussed oscillating magnetic fields $B_1$ at said Volume to polarize or tip the magnetic moments of hydrogen nuclei of fluids within rock pores. The same antenna can be used to receive signals of proton precession in the Volume of interest immediately after transmission of the RF polarizing field $B_1$. Extremely rapid damping of the antenna between the transmitting and receiving modes of operation is accomplished by a Q-switch disclosed herein. The invention provides for the direct measurement of NMR decay having transverse relaxation time $T_2$ behavior, and further provides for the fast repetition of pulsed measurements from within a borehole. An additional magnet array may be mounted offset from the first magnet configuration to prepolarize a formation before it is measured in order to pre-align a larger number of protons than the single magnet configuration could do by itself. Additional features of the invention are disclosed which increase the Signal/Noise ratio of the measured data, and improve the quality and quantity of borehole NMR measurements, per unit of time spent. Disclosed interpretation methods determine fluid flow permeability and longitudinal relaxation time $T_1$-type parameters by directly comparing the measured decay signals (such as $T_2$ or $T_2^*$ type decay) to a representation which responds to both the decay time $t_{dec}$ and the imposed polarization period prior to such decay $t_{pol}$. The parameters of amplitude and $T_1$ are determined and combined with certain preferred methods to generate robust values of formation characteristics such as fluid flow permeability. Other related methods are disclosed.

60 Claims, 15 Drawing Sheets

U.S. PATENT DOCUMENTS

| | | |
|---|---|---|
| 3,439,260 | 4/1969 | Bene . |
| 3,483,465 | 12/1969 | Baker . |
| 3,484,680 | 12/1969 | Hurlbert .............................. 324/303 |
| 3,508,438 | 4/1970 | Alger et al. .......................... 324/303 |
| 3,528,000 | 9/1970 | Schwede . |
| 3,538,429 | 11/1970 | Baker . |
| 3,597,681 | 8/1971 | Huckabay et al. ................... 324/303 |
| 3,667,035 | 5/1972 | Slichter . |
| 4,350,955 | 9/1982 | Jackson et al. ...................... 324/303 |
| 4,528,508 | 7/1985 | Vail, III . |
| 4,629,986 | 12/1986 | Clow et al. .......................... 324/303 |
| 4,665,486 | 5/1987 | Schultz ................................ 324/303 |
| 4,714,881 | 12/1987 | Givens ................................ 324/303 |

OTHER PUBLICATIONS

Farrar & Becker, "Pulse and Fourier Transform Nuclear Magnetic Resonance", *Academic Press, N.Y.*, Chapter 2, pp. 18–33.

Neuman & Brown, "Applications of Nuclear Magnetism Logging to Formation Evaluation", *Journal of Petroleum Technology*, (Dec. 1982), pp. 2853–2860.

Timur, "Pulsed Nuclear Magnetic Resonance Studies of Porosity, Movable Fluid and Permeability of Sand Stones", *Journal of Petroleum Technology*, (Jun. 1969), pp. 775–786.

McDonald & Leigh, "A New Method for Measuring Longitudinal Relaxation", *Journal of Magnetic Resonance*, vol. 9, pp. 358–362 (1973).

Kenyon, Day, Straley & Willemsen, "Compact and Consistent Representation of Rock NMR Data for Permeability Estimation", *61st Annual Technical Conference and Exhibition of the Society of Petroleum Engineers*, Oct. 5–8, 1986, New Orleans.

Seevers, "A Nuclear Magnetic Method for Determining the Permeability of Sandstones", *Society of Professional Well Log Analysts Trans.* (1966), paper L.

Jackson, "Nuclear Magnetic Resonance Well Logging", *Log Analyst*, Sep.–Oct. 1984, pp. 16–30.

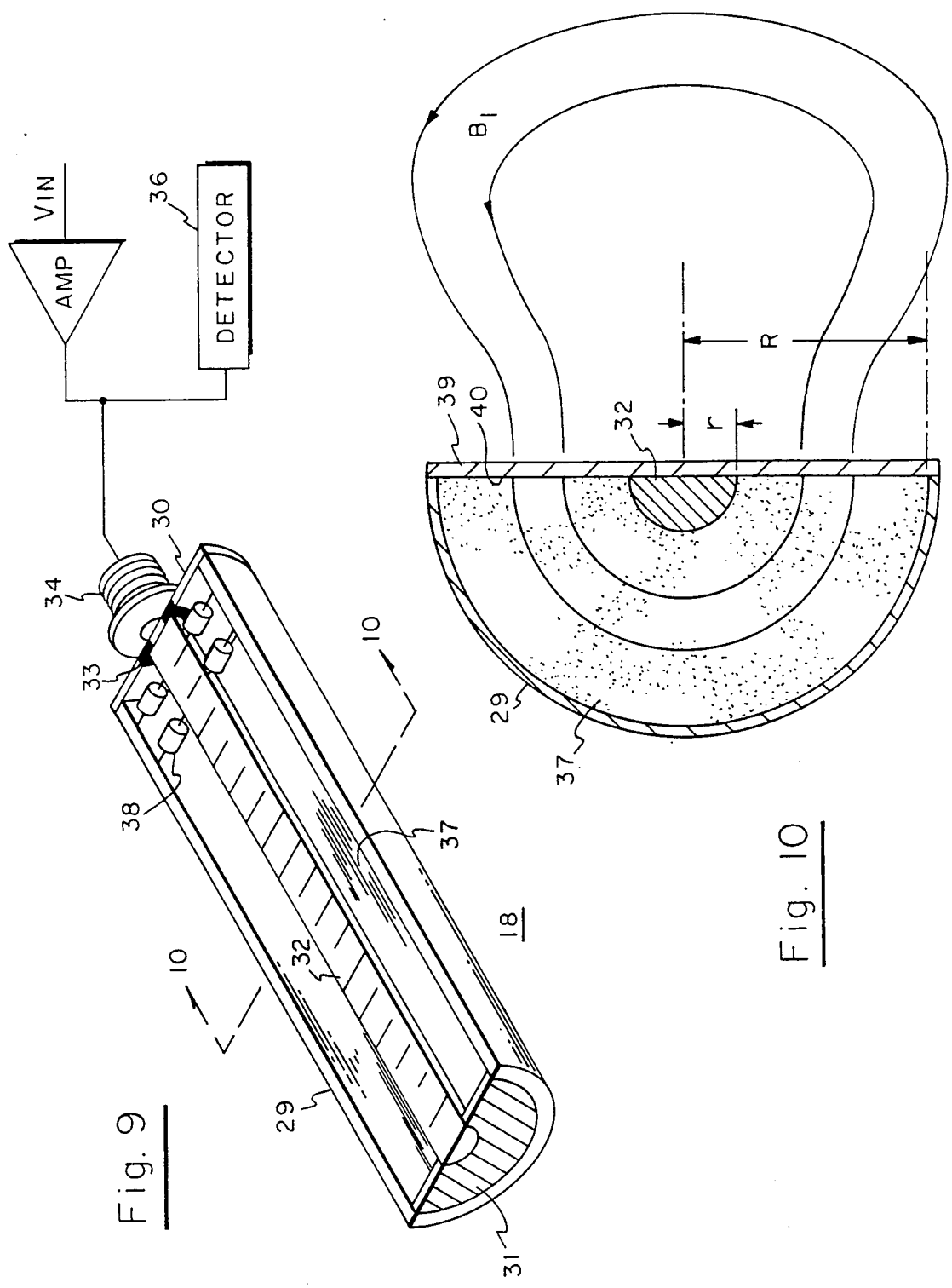

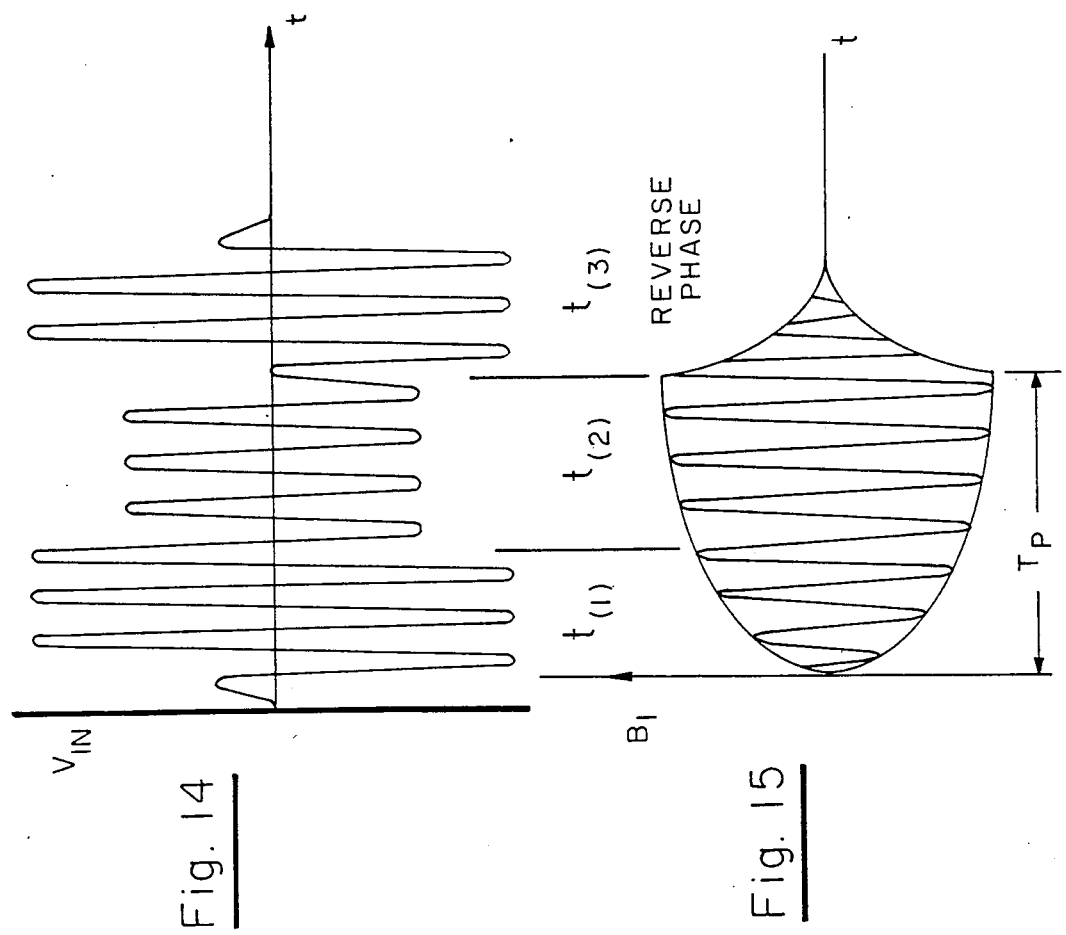
Fig. 14
Fig. 15
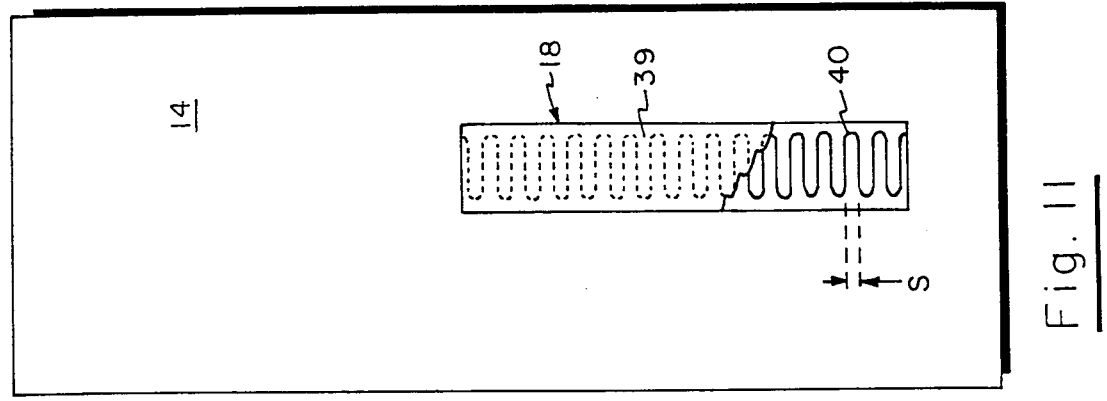
Fig. 11

BOREHOLE MEASUREMENT OF NMR CHARACTERISTICS OF EARTH FORMATIONS

This is a divisional of copending U.S. application Ser. No. 368,916, filed June 19, 1989, U.S. Pat. No. 4,933,638 which is a continuation of Ser. No. 901,084, filed Aug. 27, 1986, now abandoned.

FIELD OF THE INVENTION

This invention relates to apparatus and techniques for making nuclear magnetic resonance (NMR) measurements in boreholes, and to methods for determining magnetic characteristics of formations traversed by a borehole.

BACKGROUND OF THE INVENTION

Repeated attempts have been made to use the principles of nuclear magnetic resonance to log wells in oil exploration over the past several decades, with limited success. It was recognized that any particles of a formation having magnetic spin, for example atomic nuclei, protons, or electrons, have tendencies to align with a magnetic field which is imposed on the formation. Such a magnetic field may be naturally generated, as is the case with the earth's magnetic field $B_E$ which has an intensity of approximately 0.5 gauss in areas of the globe where boreholes are typically drilled. Any given particle in a formation is additionally influenced by localized magnetic fields associated with nearby magnetic particles, other paramagnetic materials, and the layer of ions which typically line pore walls of certain types of formations such as shales. These localized fields tend to be inhomogeneous, while the earth's magnetic field is relatively homogeneous.

The hydrogen nuclei (protons) of water and hydrocarbons occurring in rock pores produce NMR signals distinct from any signals induced in other rock constituents. A population of such nuclei, having a net magnetization, tends to align with any imposed field such as $B_E$.

When a second magnetic field $B_1$ transverse to $B_E$ is imposed on the protons by a logging tool electromagnet, the protons will align with the vector sum of $B_E$ and $B_1$ after a sufficient polarization time $t_{pol}$ has passed. If the polarizing field $B_1$ is then switched off, the protons will tend to precess about the $B_E$ vector with a characteristic Larmor frequency $\omega_L$ which depends on the strength of the earth's field $B_E$ and the gyromagnetic constant of the particle. Hydrogen nuclei precessing about a magnetic field $B_E$ of 0.5 gauss have a characteristic frequency of approximately 2 kHz. If a population of hydrogen nuclei were made to precess in phase, the combined magnetic fields of all the protons can generate a detectable oscillating voltage in a receiver coil. Since the magnetic moment of each proton produces field inhomogeneities, the precessing protons tend to lose their phase coherence over time, with a characteristic time constant called the transverse or spin-spin relaxation time $T_2$. Furthermore, field inhomogeneities are also produced by other physical phenomena as mentioned above, so that the observed dephasing relaxation time $T_2^*$ is usually shorter than $T_2$. Borehole magnetic resonance measurements of the above type are commercially available as a part of the NML† service Schlumberger Technology Corporation, Houston, Tex. († Mark of Schlumberger). This tool is capable of measuring the Free Induction Decay of hydrogen nuclei in formation fluids, and to obtain the parameters $T_1$ and $T_2^*$. It does not measure the transverse relaxation time $T_2$. A description of the basic components, operation and interpretation of the commercial logging tool used in the NML service is contained in a paper entitled, "An Improved Nuclear Magnetism Logging System and its Application to Formation Evaluation", by R. C. Herrick, S. H. Couturie and D. L. Best, presented at the *54th Annual Fall Technical Conference and Exhibition of the Society of Petroleum Engineers* (A.I.M.E., Dallas, Tex.) in Las Vegas, Nev., Sept. 23-26, 1979; this paper, appended hereto, is incorporated herein by reference.

Other sequences of magnetic fields can be imposed on a population of protons in a formation, to measure other characteristics thereof. For example, if a pulse of alternating current having a frequency f is passed through a transmitter coil, producing an oscillating polarizing field $B_1$ perpendicular to a static field $B_o$, a population of protons precessing at a Larmor frequency equal to f would tend to align at an angle to $B_1$. At the end of the pulse, when $B_1$ is removed, the aligned protons experience a perpendicular torque, and precess about the $B_o$ vector. After a characteristic time called the longitudinal or spin-lattice relaxation time $T_1$, the protons have relaxed to thermal equilibrium, wherein a weighted percentage of protons are aligned in the direction of $B_o$. Various other sequences of imposed magnetic fields can be used, as is discussed in T. C. Farrar and E. D. Becker, "Pulse and Fourier Transform Nuclear Magnetic Resonance", Academic Press, N.Y. (1971), Chapter 2, pp. 18-33, which is incorporated herein by reference.

Although measurements of NMR characteristics of rock samples can be accurately made in a laboratory, making comparable measurements in a borehole is greatly exacerbated by the hostile environment where temperatures may reach several hundred degrees Fahrenheit, pressures reach thousands of p.s.i. and all of the equipment must be packed within a cylindrical volume of only several inches diameter.

One of the earliest NMR logging tools is shown in U.S. Pat. No. 3,289,072 granted Nov. 29, 1966 to N. A. Schuster. A strong electromagnet is used to subject a sample of water or oil to a predetermined magnetic field. A RF coil produces an oscillating second magnetic field which causes nuclear magnetic resonance of protons in the sample and resonance of similar protons in the adjacent formation. Schuster proposed the use of a multipole electromagnet mounted in a wall engaging pad, or alternatively a larger electromagnet mounted within the logging sonde, to produce a static magnetic field $B_0$. Schuster has also proposed other configurations of electromagnets and detection RF coils, for example in U.S. Pat. No. 3,083,335 granted on Mar. 26, 1963, wherein the coil is positioned within a gap between two opposite poles of two bar magnets. Here, the magnetic field lines of the coil intersect field lines of the bar magnets perpendicularly, which is the optimum angle for inducing nuclear magnetic precession.

A more recent U.S. Pat. No. 3,667,035 granted May 30, 1972 to C. P. Slichter, shows a similar configuration of two coaxially aligned bar magnets and a RF coil positioned within the gap between opposite poles of the magnets. The term "bar magnet" is used herein to mean any magnet having only one north pole and one south pole, facing opposite directions, and may be either a permanent magnet or an electromagnet. Both the Slichter design and the Schuster design use electromagnets which require inconveniently large D.C. currents to be transmitted to a logging sonde through many thousands of feet of electrical cable.

U.S. Pat. No. 3,528,000 granted Sept. 8, 1970 to H. F. Schwede shows one type of NMR logging tool in FIGS. 8 and 9, wherein a permanent magnet produces a first magnetic field which is fixed in its intensity, and an inductive coil produces an oscillating magnetic field whose frequency is varied over a selected range. Since the first magnetic field is produced by two opposite magnetic poles (one N and one S) placed side by side, the field is not homogeneous and the spatial gradient of the field is evidently non-zero at all points in the formation. In addition, since the first and second fields intersect not only in the formation, but also within the borehole, it is evident that protons constituting water or hydrocarbons within the borehole fluid contributes to signals detected by the RF coil, and must be removed either electronically or by chemically treating the borehole fluid, if a true formation measurement is desired.

Other NMR logging tools have been proposed which use permanent bar magnets, aligned coaxially in a logging sonde with a detection coil positioned in the gap between the magnets, for example as shown in U.S. Pat. No. 3,597,681 granted Aug. 3, 1971 to W. B. Huckabay.

Another permanent magnet configuration has been proposed in U.S. Pat. No. 4,350,955 granted Sept. 21, 1982 to J. A. Jackson. wherein two permanent bar magnets are coaxially aligned such that the RF detection coil is positioned in the gap between two similar poles of the two magnets. Similarly, United Kingdom Patent Application No. 2,141,236-A, published Dec. 12, 1984, shows a similar configuration of coaxially aligned bar magnets with a detection coil positioned in a gap between the magnets. This type of configuration produces a toroidal region of homogeneous magnetic field wherein nuclear resonance may be measured. However, these tools may be adversely affected by signals from the borehole fluid in a large or deviated borehole where the tool would tend to lean against one side wall of the borehole. If the tool is designed to produce the toroidal region far away from the tool body, the produced magnetic field becomes much weaker, resulting in a significantly weaker signal. This configuration further requires that the detection coil or antenna be enclosed by a structure which would not block the oscillating electromagnetic waves of the measured signal. For example, fiberglass or some other non-metallic material is typically used; unfortunately, this structurally weakened link decreases the structural integrity of the tool and renders it considerably less useful in rough borehole conditions.

NMR measurement of particles other than hydrogen nuclei having magnetic spin have also been proposed. U.S. Pat. No. 3,439,260, granted Apr. 15, 1969 to G. J. Benn et al, for example, discloses techniques of measuring magnetic resonance of carbon-13 nuclei in earth formations.

Other representative U.S. patents which have been granted for NMR logging tools and techniques include the following: U.S. Pat. Nos. 3,042,855 to R. J. S. Brown; 3,508,438 to R. P. Alger et al.; 3,483,465 to J. H. Baker, Jr.; 3,505,438 to R. P. Alger, et al.; 3,538,429 to J. H. Baker, Jr.; 4,035,718 to R. N. Chandler.

Each of the NMR logging tools which have been proposed or constructed has had practical deficiencies. All of them had to deal with the fundamental difficulties of making this kind of delicate measurements under severe conditions of temperature, pressure, and physical trauma typical of logging runs in oil wells. Furthermore, since the concentration of hydrogen nuclei within the borehole is much higher than the concentration in any rock formation, the undesirable NMR signals arising in a borehole are potentially much higher than any signals from surrounding formations. In order to alleviate this troubling phenomenon, it has been known in the art to treat the borehole fluid with a paramagnetic substance such as magnetite, and to circulate the treated fluid throughout the borehole before a logging run is made so that the relaxation time of hydrogen nuclei in the borehole is shortened by so much that its contribution to the NMR measurement is eliminated. Such pretreatment of borehole fluid is expensive and time consuming. Pretreatment may also introduce the same chemical, via the borehole, into adjacent permeable formations, and thus distort measurements.

It has also been recognized that those NMR logging tools which require powerful electromagnets tend to be unreliable because the high power currents flowing through the tool inevitably tend to break down various electronic components such as switches, especially under the high temperature environment in boreholes. The previous tools all required that the sonde or pad body be constructed of a non-metallic material such as fiberglass, synthetic rubber or teflon to enable detection of A.C. signals. These materials are considerably weaker than the alloy metals which are normally used in constructing other types of logging tools. The inability to use a strong metallic superstructure in constructing NMR logging tools has further contributed to their relative unpopularity in the industry.

Previous NMR logging tools typically required approximately 20–30 milliseconds, called "dead time", after a polarizing field pulse is shut and before the transmitting coil is sufficiently damped to permit measurements to be taken. During this dead time, considerable information of magnetic relaxation is irretrievably lost, and the S/N ratio is considerably degraded.

The commercially available NMR logging tool cannot directly measure the spin-spin relaxation time $T_2$. Instead, the existing commercial tool obtains measures of the Free Fluid Index (FFI) and the observable dephasing relaxation time $T_2^*$, also called the free induction decay time constant. Various log interpretation techniques may be used to derive other useful information as discussed in, e.g. "Applications of Nuclear Magnetism Logging to Formation Evaluation" by C. H. Neuman and R. J. S. Brown, *Journal of Petroleum Technology* (December 1982) pp. 2853–2860, and in the Herrick et al. paper cited above.

For many of the above reasons, the prior logging tools have not been capable of determining formation characteristics with sufficient accuracy and dependability to become fully accepted by the industry.

Accordingly, it is an object of the present invention to provide improved apparatus and methods for determining magnetic characteristics of earth formations more accurately and more dependably.

It is an additional object of the invention to provide apparatus and methods to determine the nuclear magnetic relaxation time, the free fluid porosity, permeability and related pore fluid characteristics of earth formations traversed by a borehole.

It is also an object of the invention to provide borehole apparatus for measuring magnetic resonance which can be constructed of strong metallic materials, which can operate repeatedly in borehole conditions with high reliability, and which can accurately measure formation characteristics without requiring any pretreatment of the borehole fluid with magnetic substances.

It is a further object of the invention to provide a magnet configuration for NMR measurements which has a simple, sturdy construction, and which is easily and conveniently tested, calibrated and used in logging a borehole.

It is also an object of the invention to provide a magnetic resonance logging tool which directly measures the transverse relaxation time $T_2$ of formations traversed by a borehole.

In another aspect of the invention, it is an object to provide improved methods for determining the permeability and like parameters from measured free induction decay signals of NMR logging tools.

It is also an object of the invention to provide improved methods for determining the magnetic relaxation times of a measured population of particles in earth formations surrounding a borehole.

SUMMARY OF THE INVENTION

In accordance with the present invention, apparatus is provided which produces a static and substantially homogeneous magnetic field focussed into a formation on one side of the logging tool. By directing and configuring the combined magnetic fields of a configuration of magnets, applicants have produced a region, remote from the configuration of magnets, wherein the spacial field gradient substantially vanishes, thereby insuring that the field is highly homogeneous throughout that region. In a preferred form, the magnets are mounted within a skid or logging pad, the static magnetic field is directed through the face of the pad into an adjacent formation, and the region of substantially homogeneous field is situated in a volume of formation behind the mudcake layer which typically lines borehole walls. A homogeneous magnetic field several hundred times stronger than the earth's magnetic field can be thus imposed, or "focused", on a volume of formation in situ.

In one aspect of the present invention, the RF antenna is mounted on the outside of the metallic structure of the tool so that the tool body serves as a natural shield against any signals which may be generated by resonant conditions behind the body, particularly those potentially strong resonance signals from borehole fluid. In the preferred form, the antenna is configured to focus its signals radially outwardly from the pad face, into the volume of formation having the homogeneous sub field, thereby additionally reducing the distortion of measured signals from borehole effects. As a consequence of this distinctive feature of the invention, the logging apparatus may be constructed of strong metallic alloys, unlike prior art tools, and the present measurement technique actually uses the shielding effect of a metal sonde to good advantage, to enhance the S/N ratio of NMR measurement. Since borehole effects are excluded by the dual focussed design, it is no longer necessary to pretreat the borehole fluid with paramagnetic chemicals.

In accordance with a preferred form of the invention, an elongated trough antenna is provided on a pad face, parallel to the borehole axis and to an elongated volume of substantially homogeneous static magnetic field in the adjacent formation. By superposing the geometric shape of the volume of homogeneous and static field with the pattern of the RF field from the antenna, near optimum resonance conditions can be created. In the preferred embodiment the static field is directed radially into said volume, while the RF field is circumferentially directed and thus perpendicular to the static homogeneous field within the volume of investigation. The length of the trough antenna is preferably about equal to the length of the volume of investigation.

In accordance with the present invention, methods and apparatus are provided for making fast pulsed measurements of magnetic resonance in earth formations surrounding a borehole, particularly the direct measurement of spin-spin relaxation time $T_2$, to determine formation characteristics.

In accordance with a further aspect of the invention, the transmitting antenna is also used for receiving magnetic resonance signals, and special circuitry is used to very rapidly damp the ringing current which occurs in the antenna after a power shut-off. The special circuitry, called a Q-Switch, damps the polarizing antenna current about 1000 times faster than the previous tool, and enables many pulses to be injected successively into a formation in a short period of time.

By vastly increasing the number of measurement cycles per unit time, the present invention enables the logging tool to: (1) increase the S/N of the overall measured data set, thereby permitting either a faster logging rate or continuous logging, and (2) reduce the NMR measurement time during which nuclei may diffuse within rock pores, thereby reducing the undesirable magnetic effects of such diffusion.

In accordance with another aspect of the invention, additional apparatus is provided to prepolarize a formation volume of interest before the main magnetic configuration reaches proximity to the formation. The prepolarization field is preferably much stronger than that of the main magnet configuration, and serves to increase the population of protons that is aligned in the $B_0$ vector direction, and thus further increases the magnetic precession signal level.

In accordance with yet another aspect of the invention, small currents are introduced in the vicinity of a measuring tool to alter the static field during part of the measurement cycle to spoil the signals from these localized regions. In the preferred embodiment, the small currents flow through a wire preferably configured as a loop covering the antenna opening and attached parallel to the wall-engaging face of the tool. This configuration serves to significantly reduce or eliminate any resonance signals produced by borehole mud or mudcake immediately adjacent to the antenna surface, and substantially reduces undersirable signals. The spatial extent and magnetic effects of these field inhomogeneities can be carefully controlled by selecting the spacing of adjacent sectors of the wire, the current, and other relevant dimensions. In a different aspect of the invention, the wire or its equivalent can be used to produce magnetic field gradients extending into the volume of measured resonance, which permits other advantageous magnetic measurements to be made.

For other objects and advantages of the invention, and to provide a fuller understanding thereof, reference is made to the following description taken in conjunction with the cited references and the accompanying drawings.

BRIEF DESCRIPTION OF THE DRAWINGS

FIG. 9 is a prespective view of an antenna in accordance with the present invention;

FIG. 10 is an enlarged cross-sectional side view of the antenna shown in FIG. 9;

FIG. 11 is an enlarged front view of the wall engaging face of the logging tool shown in FIG. 1, partially cut away to show the antenna and a meandering wire of the present invention;

FIG. 14 is a diagram showing representative signals input to the amplifier shown in FIG. 9 and FIG. 12;

FIG. 15 is a diagram showing the pulse shape of an exemplary oscillating magnetic field $B_1$ produced by the antenna of FIG. 9;

DESCRIPTION OF PREFERRED EMBODIMENTS

Figure 1:
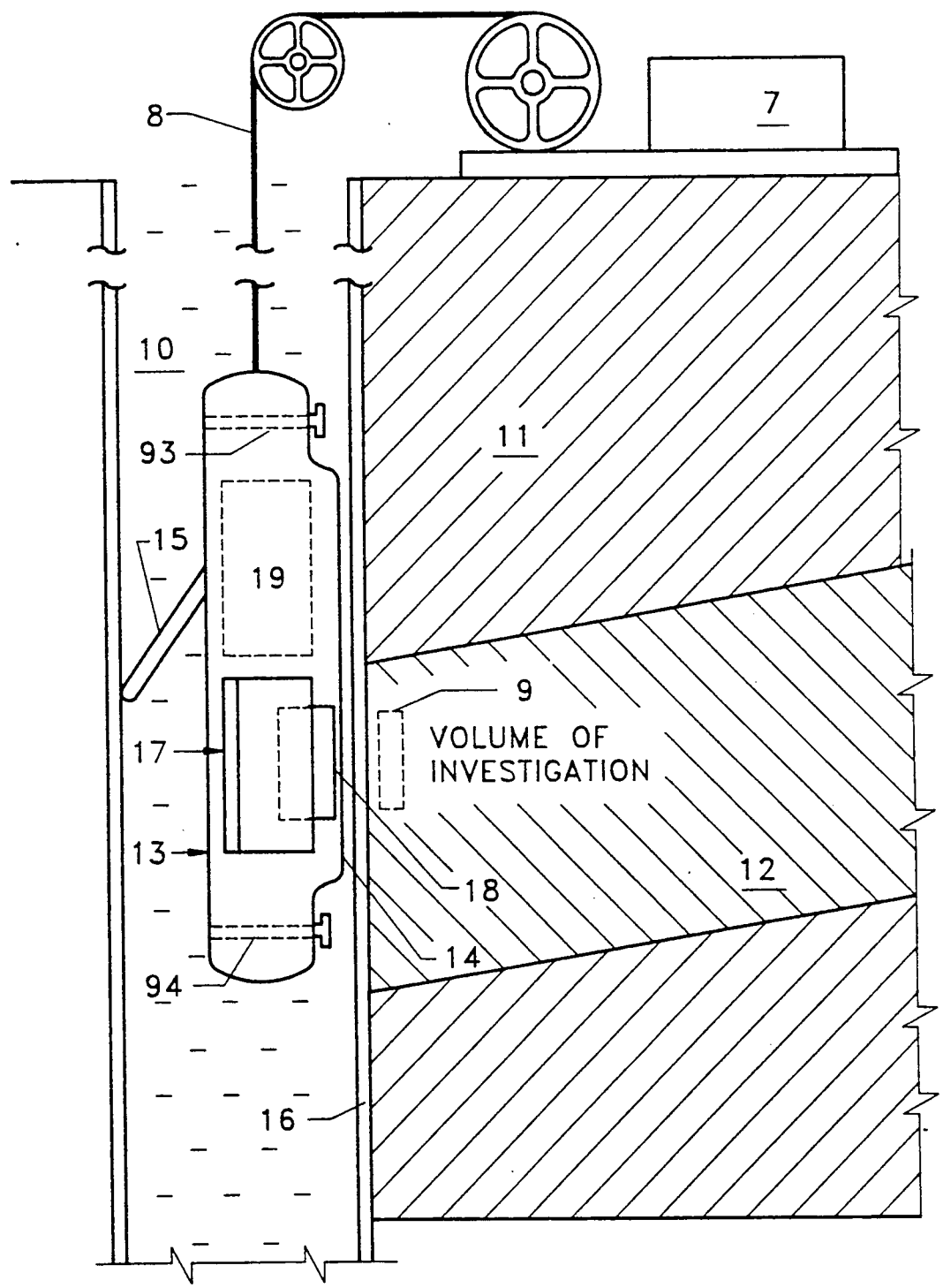
FIG. 1 is a side view of a NMR logging tool positioned in a borehole for making measurements of surrounding formations, in accordance with the present invention.

Referring to the drawings and particularly FIG. 1 thereof, a borehole 10 is shown adjacent to formations 11, 12, the characteristics of which are to be determined. Within borehole 10 there is shown a logging tool 13 connected via a wireline 8 to surface equipment 7. Tool 13 preferably has a face 14 shaped to intimately contact the borehole wall, with minimal gaps or standoff. The tool 13 also has a retractable arm 15 which can be activated to press the body of the tool 13 against the borehole wall during a logging run, with the face 14 pressed against the wall's surface.

Although tool 13 is shown in the preferred embodiment of FIG. 1 as a single body, the tool may obviously comprise separate components such as a cartridge, sonde or skid, and the tool may be combinable with other logging tools as would be obvious to those skilled in the art. Similarly, although wireline 8 is the preferred form of physical support and communicating link for the invention, alternatives are clearly possible, and the invention can be incorporated in a drill stem, for example, using forms of telemetry which may not require a wireline.

The formations 11, 12 have distinct characteristics such as formation type, porosity, permeability and oil content, which can be determined from measurements taken by the tool. Deposited upon the borehole wall of formations 11, 12 is typically a layer of mudcake 16 which is deposited thereon by the natural infiltration of borehole fluid filtrate into the formations.

In the preferred embodiment shown in FIG. 1, tool 13 comprises a magnet array 17 and an antenna 18 positioned between the array 17 and the wall engaging face 14. Magnet array 17 produces a static magnetic field $B_0$ in all regions surrounding the tool 13. The antenna 18 produces, at selected times, an oscillating magnetic field $B_1$ which is focussed into formation 12, and is superposed on the static field $B_0$ within those parts of formation opposite the face 14. The Volume of Investigation of the tool, shown in dotted lines in FIG. 1, is a vertically elongated region directly in front of tool face 14 in which the magnetic field produced by the magnet array 17 is substantially homogeneous and the spatial gradient thereof is approximately zero.

A prepolarizing magnet 19, shown in dotted lines, may be positioned directly above the array 17 in a modified embodiment of the invention which will be separately discussed.

The tool 13 makes a measurement by magnetically tipping the nuclear spins of particles in formation 12 with a pulse of oscillating field $B_1$, and then detecting the precession of the tipped particles in the static, homogeneous field $B_0$ within the Volume of Investigation, over a period of time. As seen in FIG. 1, this Volume of Investigation does not overlap the surface of the wall engaging face 14 as in some previous logging tools, and does not overlap the mudcake 16 on the borehole wall.

In a pulse echo type of measurement, as discussed in detail in the previously cited book of Farrar and Becker, for example, a pulse of RF current is passed through the antenna 18 to generate a pulse of RF field $B_1$ where the RF frequency is selected to resonate only hydrogen nuclei subjected to a static field strength equal to the field $B_0$ within the Volume of Investigation. The signals induced in antenna 18 subsequent to the RF pulse represent a measurement of nuclear magnetic precession and decay within the Volume, automatically excluding any undesirable contributions from the borehole fluid, mudcake, or surrounding formations where the field strength of $B_0$ is different.

In devising the preferred embodiment of the invention, applicants have sought to optimize the signal-to-noise (S/N) ratio of the measurement process. As will be appreciated by those skilled in the art, the following dicussion helps to explain the principal parameters to be considered in making the preferred embodiments of the invention.

Figure 2:
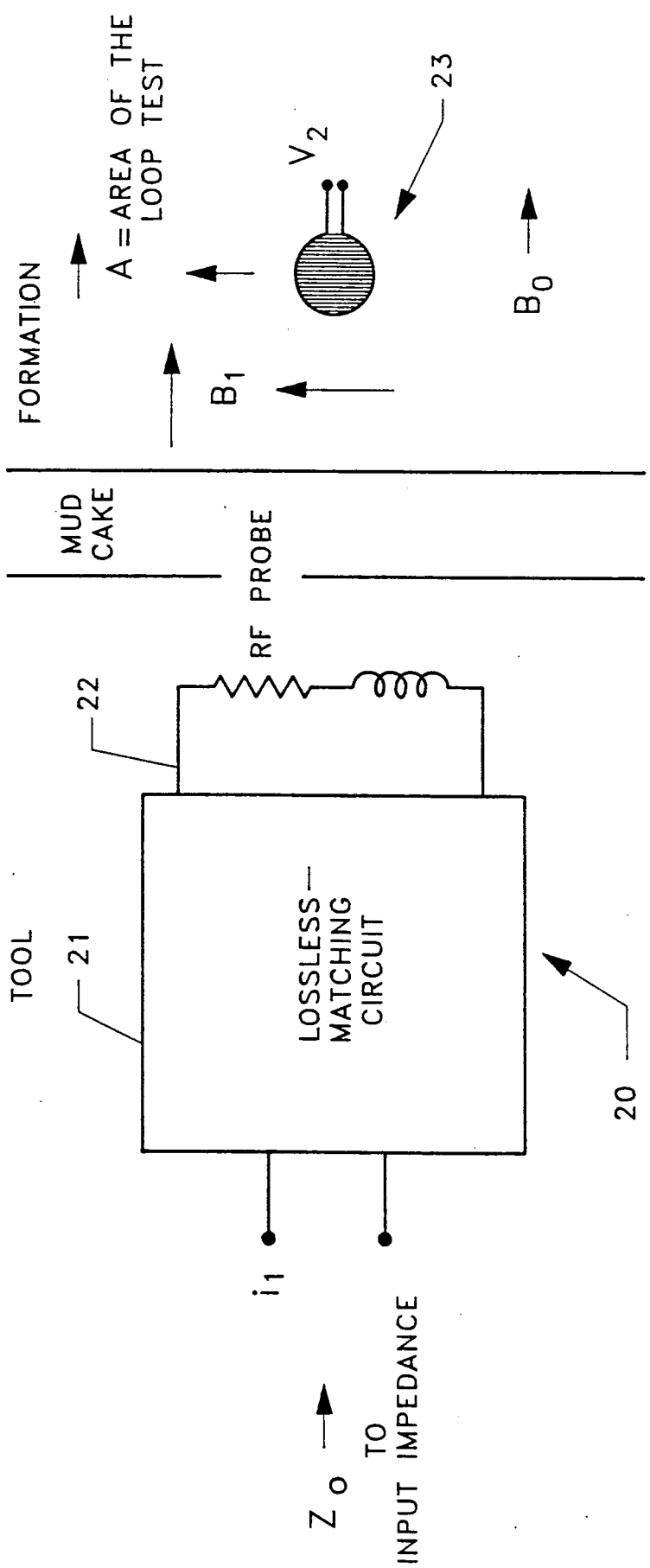
FIG. 2 is a conceptual schematic diagram representing the measurement system of the tool of FIG. 1.
Figure 3:
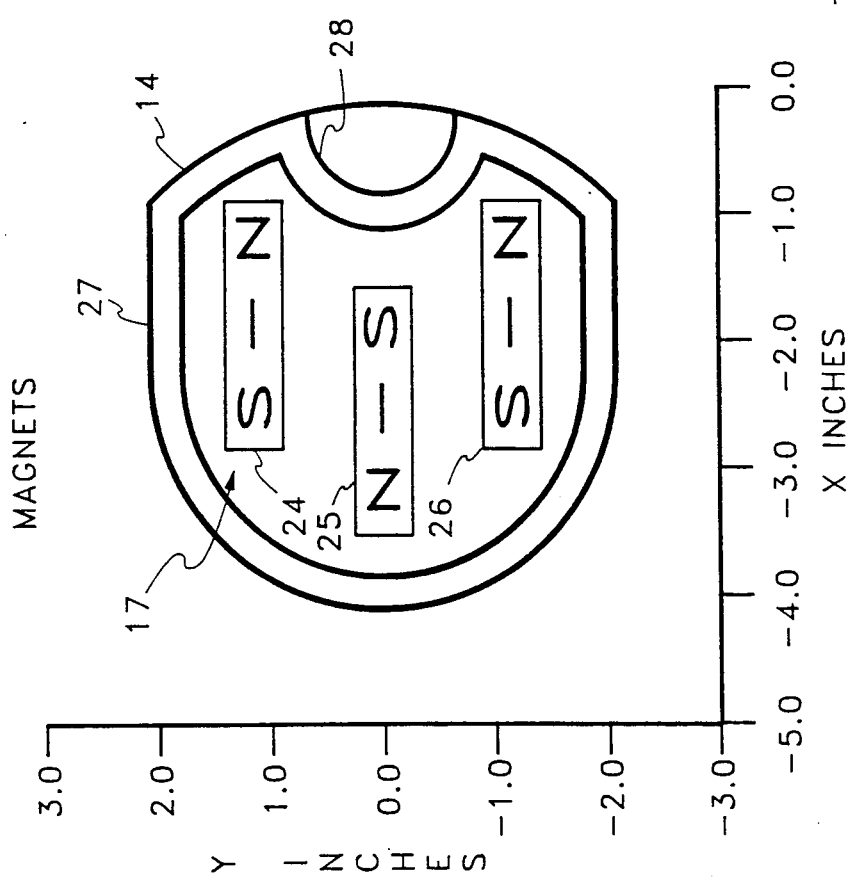
FIG. 3 is an enlarged cross-sectional plan view of a magnet array used in the preferred embodiment of the present invention shown in FIG. 1.

Referring to FIGS. 2 and 3, in considering the signal strength of a nuclear magnetic resonance measurement made by tool 13 in the adjacent formation 12, it is helpful to treat the interaction of the antenna 18 with the magnetic moment of the formation as parts of a single four terminal network to which the Reciprocity Theorem can be applied. The network 20, having an input impedance $Z_o$, comprises a lossless matching circuit 21 and an RF probe or antenna 22 which is shown simply as having a resistance and inductance in series. An oscillating current $I_1$ of frequency $\omega$ flows through RF probe 22, producing an oscillating magnetic field $B_1$ in the formation including the Area within a test loop 23. The voltage that is induced in test loop 23 as a result of the current $I_1$ is given by $$V_2 = Z_{21} I_1 = -i\omega A \cdot B_1 \tag{1}$$

where $Z_{21}$ is the cross impedance between the antenna current and the voltage induced in the test loop 23.

Now assume that a current $I_2$ is impressed upon the test loop, and induces a voltage $V_1$ at the terminals of the matching network 20, which is $$V_1 = Z_{12} I_2 \tag{2}$$

Where $Z_{12}$ is the cross impedence between the test loop current and the voltage induced in the antenna 22. Invoking the Reciprocity Theorem, $Z_{12} = Z_{21}$, we obtain.

$$V_1 = -i\omega A \cdot \left(\frac{B_1}{I_1}\right) I_2. \tag{3}$$

Since the magnetic moment of the loop 23 is $m = I_2 A$, the magnetization $dM$ of a volume $dV$ is $dM = I_2 A \, dV$. The net signal from the entire formation can be derived from the above and represented as $$V_S = -i \int dV \omega M \cdot \left(\frac{B_1}{I_1}\right) \tag{4}$$

where the integral is taken over the volume in which the resonance condition $B_0 = \omega/\gamma$ is satisfied. In order to optimize the measured signal response of the present NMR tool, we may assume that the volume of NMR investigation has an area $A_R$ and a length $L$, and that the integrand is constant within this volume. In practice, we have found this assumption to be a fairly good approximation. By making the substitutions $\omega = \gamma B_0$ and $M = \chi B_0/\mu_0$ in the above equation, where $\gamma$ is the gyromagnetic ratio, $\mu_0$ is the magnetic permeability of free space, and $\chi$ is the nuclear magnetic susceptibility of protons in the formation we derive $$V_S = \frac{X Y}{\mu_0} B_0^2 \left(\frac{B_1}{I_1}\right) A_R L. \tag{5}$$

Now we want to estimate the size of the area $A_R$ for actual magnetic configurations such as that of the magnet array 17 shown in FIG. 1. As will be further discussed hereinbelow, magnet array 17 produces a static magnetic field $B_0$ having a saddle point at the center of a homogeneous field region designated as the volume 9 in FIG. 1. The field strength may be approximated by the Taylor Series expansion $$B(x,y) = B_0 + \frac{1}{2} \frac{\partial^2 B_0}{\partial x^2} (x^2 - y^2) \tag{6}$$

Noting that the resonance condition in pulse NMR is met when the deviation of the static field from its center value, $B_o(x,y) - B_o(0,0)$ is no greater than half the magnitude of the RF field $B_1$, the area of the resonant region can be derived to be approximately $$A_R = 4 \frac{B_1}{\partial^2 B_0/\partial x^2} \tag{7}$$

after making the simplifying assumption that the area has a square cross-section. This and other approximations are made here to more simply illustrate the principles underlying the invention, it being understood that other more exact derivations are obviously possible. Making substitutions for the above equation (5) for the measured NMR signal, we obtain $$V_S = \frac{4XY}{\mu_0} \frac{B_0^2}{\partial^2 B_0/\partial x^2} \left(\frac{B_1}{I_1}\right)^2 I_1 L. \tag{8}$$

It is clear from the qualitative relationships of equation (8) that the measured NMR signal can be made better or worse by changing the various parameters given. However, increasing the signal level is not sufficient, and it is highly desirable to keep the thermal noise level as low as possible, relative to the signal $V_S$. The root mean square thermal noise is $$V_N = (4\kappa T Z_0 \Delta f)^{\frac{1}{2}} \tag{9}$$

where $Z_0$ is the input impedance of the matching network 20 (nominally 50 ohms), $\kappa$ is Boltzman's constant, and $\Delta f$ is the measurement bandwidth, which is matched to the bandwidth of the population of resonated particles in the formation, $\gamma B_1/2\pi$. The following ratio of the peak signal to the root mean square noise is obtained;

$$\frac{V_S}{V_N} = \tag{10}$$

$$\frac{2X}{\mu_0} \left(\frac{\Pi Y}{\kappa T}\right)^{1/2} \left(\frac{B_0^2}{\partial^2 B_0/\partial x^2}\right) \left(\frac{B_1}{P_1^{1/2}}\right)^{3/2} P_1^{1/4} L$$

In equation (10) the power fed to the antenna, $P_1$, has been substituted for the current using the relationship $P_1 = I_1^2 Z_0/2$. Further, using the conventional definition of the Curie Law susceptibility in MKS units, $$\chi = \mu_0 \frac{N\phi Y^2 I(I+1) \hbar^2}{3\kappa T}, \tag{11}$$

we obtain the final expression for the signal-to-noise (S/N) ratio $$\frac{V_S}{V_N} = \left[ \frac{2}{3} (\pi)^{1/2} N\phi Y^{5/2} I(I+1) h^2 \left( \frac{1}{\kappa T} \right)^{3/2} \right] \left[ \left( \frac{B_0^2}{\partial^2 B_0/\partial x^2} \right) \left( \frac{B_1}{P_1^{1/2}} \right)^{3/2} P_1^{1/4} L \right] \quad (12)$$

In equation (12), the first bracketed expression above depends on environmental parameters such as the proton spin density of the fluid N, porosity $\phi$, and absolute temperature T. Some of the other terms are Planck's constant (over $2\pi$) $h$, and the nuclear spin I which has a value of $\frac{1}{2}$ for protons. The second bracketed expression contains design parameters which optimize tool performance. For example, it is readily seen that a high static field $B_0$, being a squared term, can immensely improve the S/N ratio.

Furthermore, it is seen that the expression $(B_1/P_1^{\frac{1}{2}})^{3/2}$ which is related to the "Q" of the antenna, should be made large. However, S/N cannot be indefinitely increased by increasing $B_1/P_1^{\frac{1}{2}}$ because equations (10) and (12) hold only when the bandwidth is limited by $\gamma B_1/2\pi$, e.g. when $Q < B_0/B_1$. In contrast, when $Q > B_0/B_1$, the bandwidth is $\Delta f = \gamma B_0/2\pi Q$, and equation (12) becomes $$\frac{V_S}{V_N} = \left[ \frac{2}{3} (\pi)^{\frac{1}{2}} N\phi Y^{5/2} I(I+1) h^2 \left( \frac{1}{kT} \right)^{3/2} \right] \left[ \frac{B_0^{5/2}}{\partial^2 B_0/\partial x^2} \cdot \frac{B_1}{P_1^{\frac{1}{2}}} \cdot \frac{1}{Q^{\frac{1}{2}}} \cdot L \right] \quad (13)$$

For a set antenna geometry and measurement point, it is known that the quantity $B_1/P_1^{\frac{1}{2}}$ is directly proportional to $Q^{\frac{1}{2}}$. It is seen from the above that further decreasing the losses of the antenna beyond the point where $Q > B_0/B_1$ would not increase S/N.

Referring to FIGS. 1 and 3, the magnet array 17 consists of three samarium cobalt permanent magnets 24, 25, 26, which are mounted parallel to each other within a metal alloy body 27. Magnets 24, 25, 26 are elongated in the direction longitudinally of the borehole, and measure 12 inches in the preferred embodiment. The magnetic poles of the magnets are not on the smallest faces of the slab, commonly viewed as the ends of a bar magnet; instead, the poles appear on the two opposing edges of the slab magnet and point to the left and right, respectively, in both FIG. 1 and FIG. 3. Thus, within the formation 12, the magnetic field $B_0$ surrounding the magnets remains fairly constant along the longitudinal direction of the borehole axis.

Magnets 24,25,26 should be as strong as practical, and should be capable of withstanding physical shock without disintegration. The samarium cobalt magnets that have been used, for example, are preferably enclosed in a sturdy brass casing to prevent any explosive fragmentations in the event the magnet cracks or breaks. These magnets are commercially available, and have a residual induction of typically 10,500 gauss. It would be obvious to those skilled in the art that other magnets may be substituted for the samarium cobalt magnets herein, and the slab magnets can have other dimensions than that shown in the preferred embodiment.

It is preferable to use elongated slab magnets to produce a static field in formation 12 which is constant over a substantial distance L along the z coordinate parallel to the borehole axis. A large L improves S/N and also facilitates continuous logging along the z coordinate. However, the magnets should not be so long as to make the tool 13 structurally unwieldy or to cause excessive standoff between the face 14 and the borehole wall in washed out zones.

Magnets 24, 26 are symmetrically mounted in the two sides of the body 27 with the north poles facing the same directions. Magnet 25 is positioned parallel to and between the other two magnets, but with its north poles facing oppositely from magnets 24, 26. Magnet 25 is also shifted slightly away from face 14, relative to magnets 24, 26. As shown in FIG. 3, the north poles of magnets 24, 26 point in the direction of the face 14 of the tool, while the north pole of magnet 25 is pointed away from the face 14, although the configuration obviously may be reversed and still produce a similar result.

Figure 6:
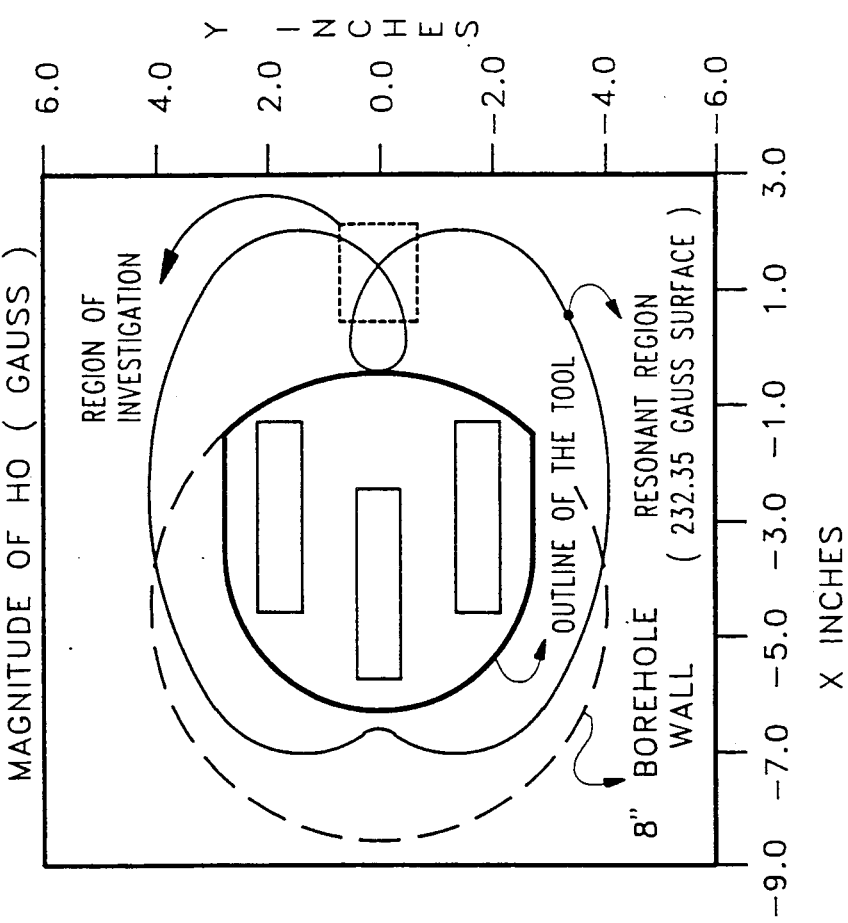
FIG. 6 is a diagram showing the magnetic field $B_0$ equal-magnitude line of 232 gauss, as in FIG. 3–5, also showing the region of investigation of the preferred embodiment shown in FIG. 1.
Figure 4:
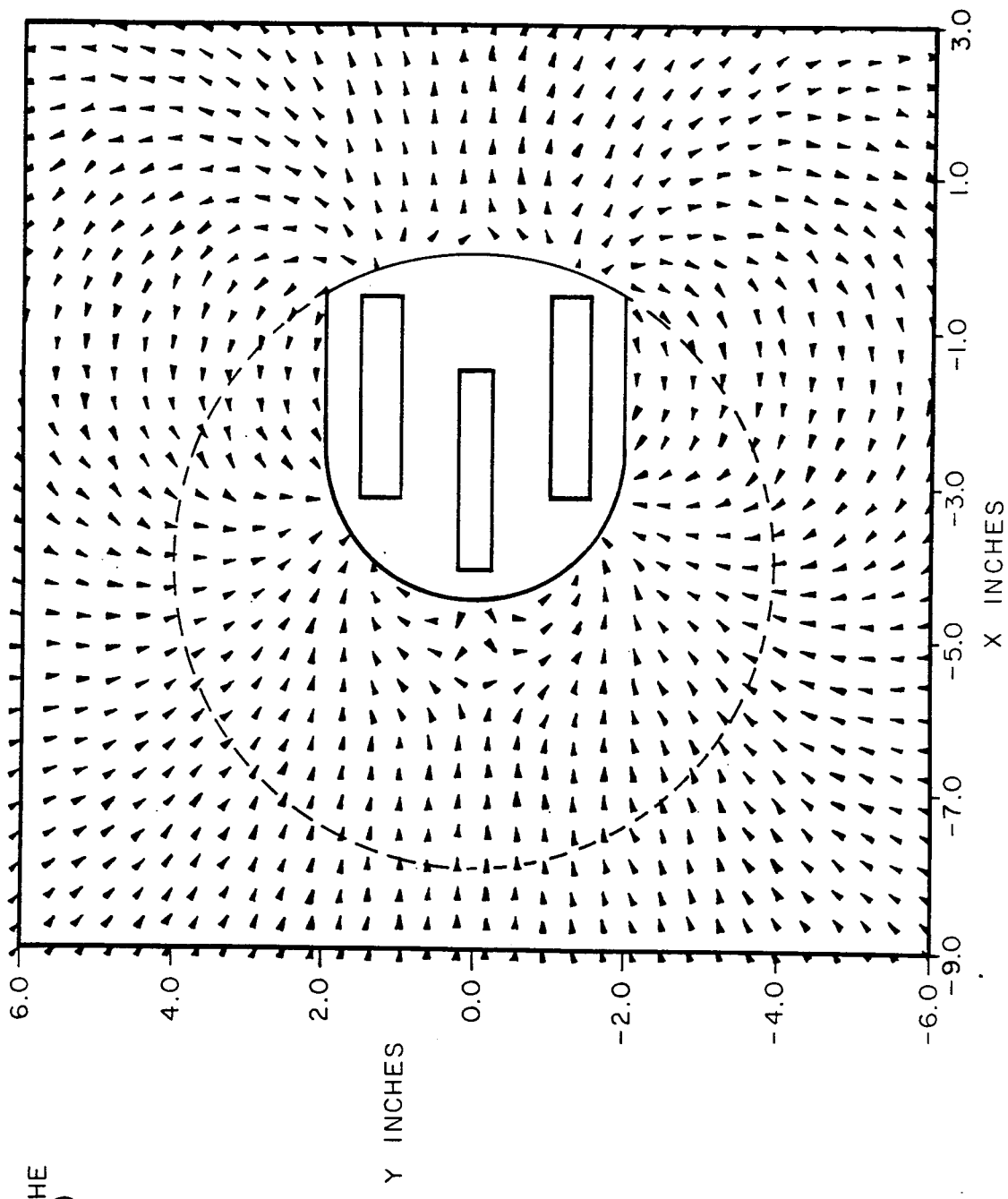
FIG. 4 is a diagram showing the magnetic field lines, represented by arrowheads, surrounding the magnet array of FIG. 3, when placed within a borehole.
Figure 5:
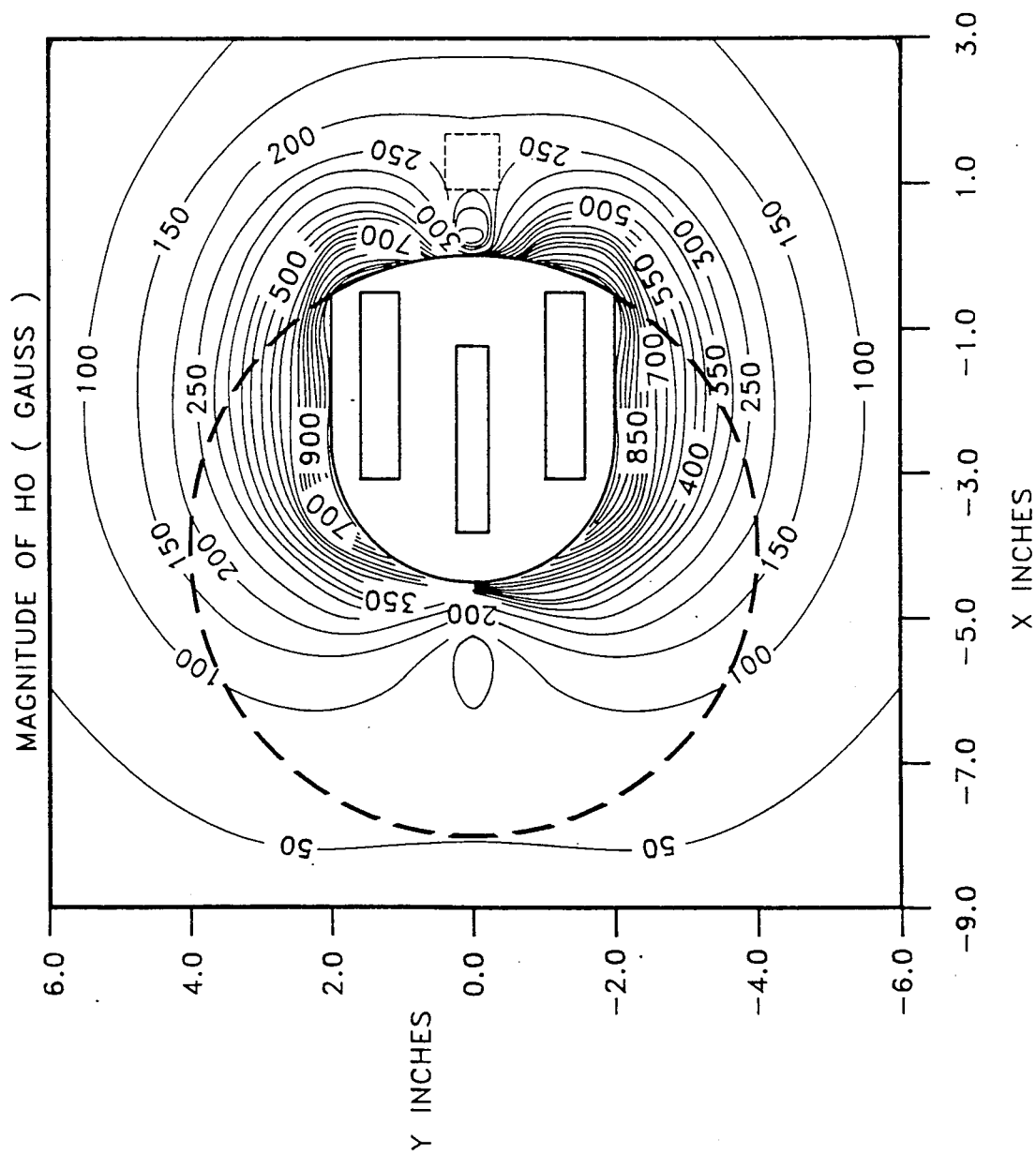
FIG. 5 is a diagram showing, in cross-section, magnetic field $B_0$ equal-magnitude lines of the magnet array shown in FIGS. 3 and 4.

Referring to FIGS. 4-6, it can be seen that, by configuring the two N poles of magnets 24, 26 to point at the face 14 and the formation 12 lying beyond, magnet array 17 would appear at a great distance like a magnetic N pole. However, the reversed pole positioning of magnet 25 substantially alters the magnetic field at close and intermediate distances into formation 12. At intermediate distances, this preferred configuration of magnet array 17 produces an interesting and important field anomaly within a uniquely defined volume directly in front of the tool face 14. As seen in greater detail in FIGS. 5-7 there is a well-defined volume in which the magnetic field is substantially constant, and wherein the spatial gradient of $B_0$ substantially vanishes. This is the primary resonance region for NMR measurements and is the Volume of Investigation shown in FIG. 1.

Figure 8:
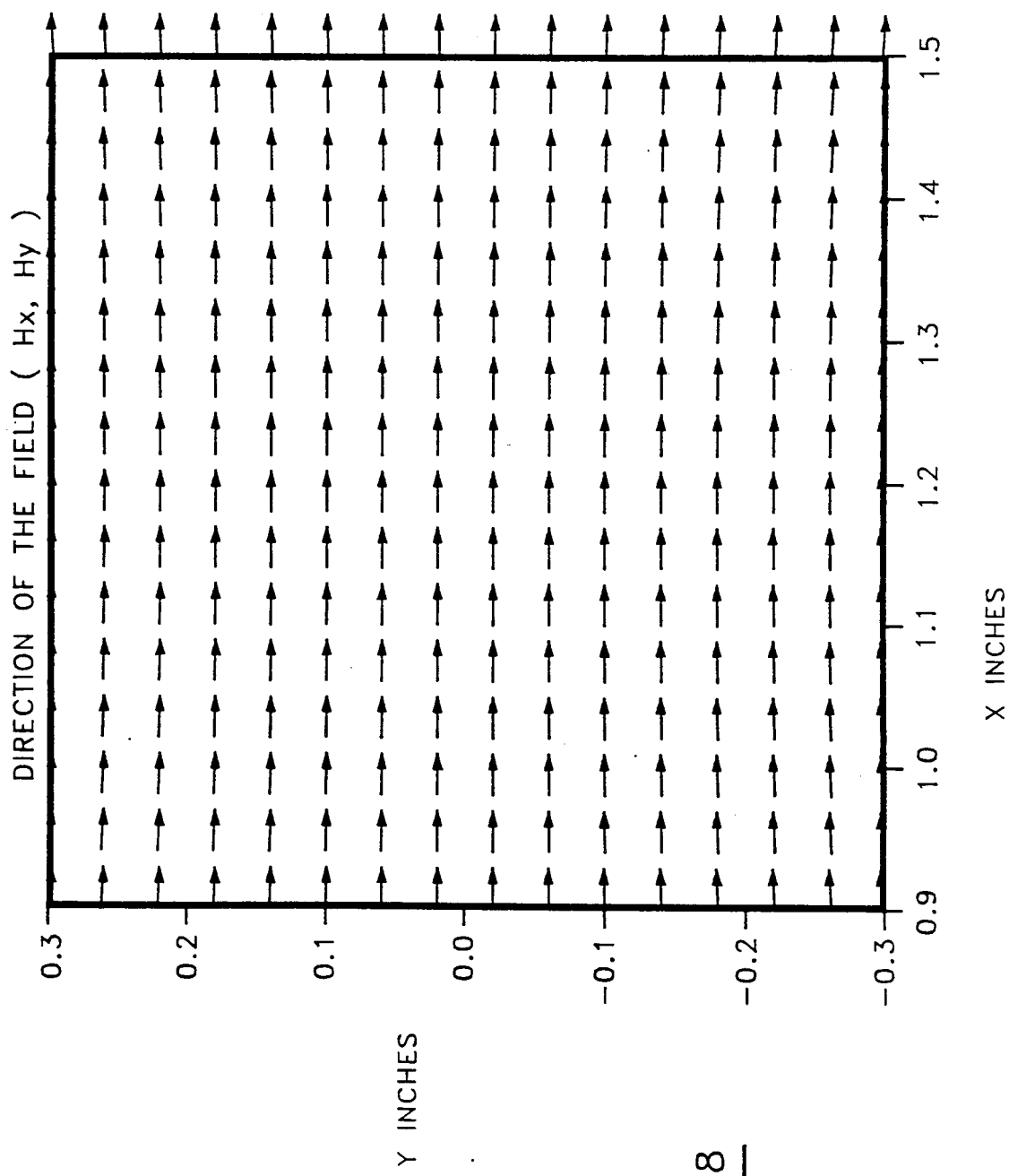
FIG. 8 is a diagram of magnetic field lines showing the vector directions and magnitude of $B_0$ within the region of investigation of FIG. 6.

FIG. 8 shows vector arrows which follow field lines within the cross sectional area approximately one inch from the tool face 14, with the length of each vector arrow proportional to field strength and the direction of each arrow following the field lines. It can be seen that the field $B_o$ projects radially into the formation and that it is quite uniform throughout this area, and has a substantially constant field strength of approximately 232 gauss.

Although the volume of greatest field homogeneity is centered about a point approximately 4/5 inch away from the wall engaging face 14, this volume of substantially homogeneous field can be shifted either a greater or less distance into the formation, depending on the relative positioning, spacing, and field strength of magnet 25 with respect to magnets 24, 26. It is additionally possible, in other embodiments of the invention, to provide for shifting of magnet 25 within the body 27 during operation of the tool so as to obtain a variable depth of investigation, depending on the circumstances. For example, if a formation having high rugosity or an extremely thick mudcake is encountered, the logging engineer may shift the position of magnet 25 a predetermined distance to the right, as seen in FIG. 3 so that the volume of investigation 9 is shifted further into the formation, to avoid obtaining undesirable resonance signals from the mudcake. However, in the preferred embodiment shown in the figures, magnets 24, 25, 26 are rigidly mounted in position since the resultant positioning of the volume 9 already avoids any substantial overlap with the relatively thin mudcake layer of typical boreholes.

Referring again to FIGS. 5, 6 and 7 it can be appreciated that the size of the Volume of Investigation 9 can depend on the nature of the measurement that is taken and the strength of a RF pulse that is transmitted by the antenna 18 as explained hereinbelow.

The metal body 27 has, on the front face 14 thereof, a semi-cylindrically shaped cavity or slot 28 which faces formations engaged by the face 14. The cavity 28 is adapted for receiving the RF antenna 18, as will be further described below. It is already clearly seen, however, that antenna 18 is positioned outside of the metal body 27 of the tool, and is automatically shielded from electromagnetic communication with regions of the borehole which lie behind the body 27, or regions of other formations in directions intercepted by the body 27. Antenna 18 is thus responsive only to magnetic fields originating in front of the wall engaging face 14, e.g. fields originating in the formation 12 or in the mudcake or mud which contacts face 14 in the vicinity of the antenna 18. By utilizing the relative geometric positioning of the antenna and the metal body 27, it is possible to minimize undesirable signal contributions which would otherwise be difficult to eliminate by other means. In the preferred embodiment, body 27 is made of metal alloy sheathing, rigidly attached to interior metal bracing, which envelops most components of the tool other than the antenna 18, including the circuitry, the magnet array 17, and the hydraulics system of the arm 15. It is also possible for the body 27 to be constructed of other combinations of materials such as composite resins, steel, etc., as long as the overall structure is sufficiently strong, and the magnetic field of the magnet array 17 can penetrate and enter the adjoining formation 12.

Antenna 18 is used both as a RF transmitter to produce a polarizing magnetic field in formation 12, and as a receiving antenna to detect coherent magnetic signals emanating from precessing protons immediately after the polarizing field is terminated. Antenna 18 should be constructed of one or more current carrying loops which are highly efficient in generating magnetic fields in the formation. It is preferably made of a current loop which produces an oscillating field $B_1$ within the volume of investigation which is perpendicular to $B_o$. Other current loop orientations may be useful in other embodiments of the invention having a static field $B_o$ differing from that of the preferred magnet array 17.

Antenna 18 is attached to body 27 and fitted within the slot 28. Its efficiency can be ideally maximized when the current density within the slot 28 is made uniform. In practice, optimum antenna efficiency is difficult to achieve, because of various electromagnetic parasitic effects like the "skin effect", the mutual inductive effects between distinct current loops, and electrical effects within individual conductors. The preferred antenna 18 pursuant to the invention comprises a single current loop, in the shape of a trough or slot, as shown in FIG. 9.

Referring to FIG. 9, the antenna 18 comprises a highly conductive semi-cylindrical cavity or trough 29, end plates 30, 31, and antenna element 32 which extends from one end plate 30 to the other end plate 31, parallel to and centered in the semi-cylindrical trough 29. The trough 29, end plates 30, 31 and antenna element 32 are all preferably made of heavy gauge copper which has extremely low electrical resistance. Antenna element 32 is insulated from end plate 30 by a non-conducting bushing 33 and is connected to an electrical mounting 34 on the other side of end plate 30. Antenna element 32 is attached at its other end to the other end plate 31 so that current passes freely between trough 29 and antenna element 32 via end plate 31. Electrical mounting 34 is shown in FIG. 9 schematically as being connected to circuitry including an amplifier 35 and a detector 36. All connections in antenna 18 are brazed or silver soldered, to ensure a suitably low resistive loss.

RF antenna 18 can be driven by amplifier 35 during specified periods of time, during which it serves as an RF antenna transmitter. Alternatively, at other specified times, antenna 18 is electronically connected to detector 36, during which time it serves as an RF receiving antenna. In certain modes of operation, antenna 18 may be called upon to alternately function as transmitter or receiver in very rapid succession.

The space between trough 29 and antenna element 32 is preferably filled with a nonconductive material 37 having high magnetic permeability. In order to increase the antenna sensitivity Ferrite materials are preferably used. Several tuning capacitors 38 are connected between the base of antenna element 32 and the trough 29, with the capacitances thereof being chosen to produce a LC circuit, with the resonant frequency being the Larmor frequency $\omega_L = \gamma B_o$.

Referring to FIG. 10, the relative dimensions of antenna 18 should be selected to maximize the antenna efficiency. The slot element radius R should be as large as practical, and the spacing R-r should be maximized subject to the condition that r must not be so small as to increase the antenna impedance excessively. It has been found that for a 12 inch trough antenna without ferrite filling, R=0.75 inch and r=0.2 inch produces optimum efficiency. A ferrite filled trough antenna having dimensions R=0.75 inch and r=0.3 inch has been found to be optimum. The length L of the antenna may be the same as the length of the magnet array 17, which is 12 inches in the preferred embodiment, but antenna 18 is preferably about the same length as the resonance region produced by the magnet array 17 in the formation, which is approximately 4 to 8 inches long.

The field $B_1$ produced by antenna 18 is an oscillating magnetic field having a frequency $f$ equal to the resonance frequency of hydrogen nuclei in the sensitive volume of formation where the static field is about 232 gauss. Therefore, $f = (\gamma B_0)/2\pi = 1.0$ MHz. The strength of $B_1$ has direct impact on the bandwidth of precessing nuclei which are resonated by $B_1$ in accordance with the bandwidth formula:

$$\Delta f = (\gamma B_1)/2\pi$$

Since the static field $B_o$ is about 232 gauss in the preferred embodiment, and the antenna generated field strength $B_1$ at 1 inch is 3 gauss, the resultant bandwidth of $B_o$ within the desired volume is also 3 gauss.

Figure 13:
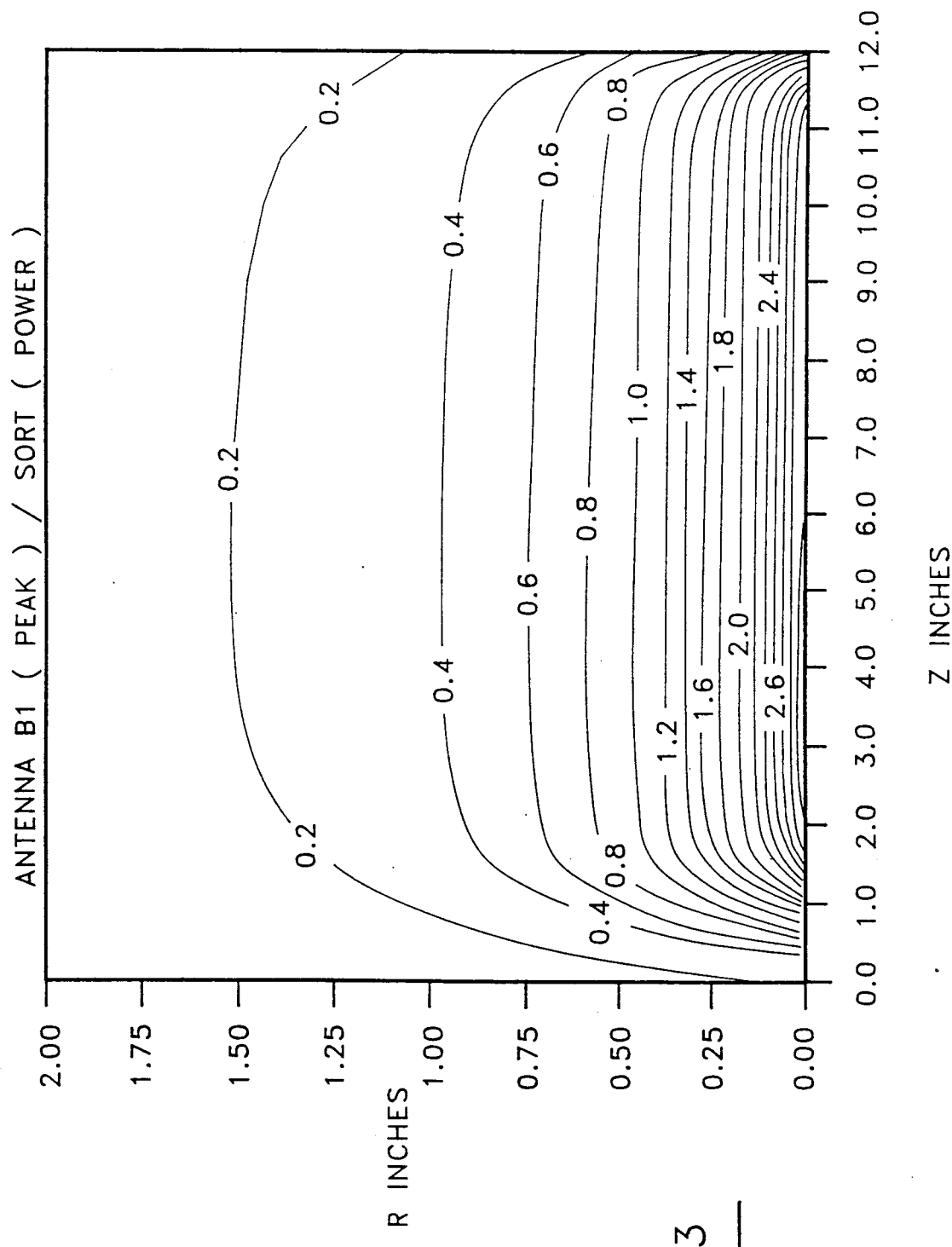
FIG. 13 is a graph of the ratio $B_1$ divided by the square root of the power $P_1$ fed to a preferred embodiment of the antenna of the invention, as in FIG. 1.

The strength of the $B_1$ field in the sensitive volume also affects the S/N ratio (equation 12) in accordance with the term $B_1/P_1^{\frac{1}{2}}$, where $B_1$ is perpendicular to the static $B_o$ field. FIG. 13 shows a plot of the magnitude of $B_1/P^{\frac{1}{2}}$ in front of a 12" trough antenna, where $P_1$ is the power applied to a 50 ohm impedance matching network of the antenna 18 and B1 is the circularly polarized component of the radiated field. It is seen that the field strength is quite constant at 1 inch for a longitudinal distance of about 8 inches.

Referring to FIGS. 3, 10, and 11, antenna 18 is installed in slot 28 and covered with a wear plate 39 made of a non-conductive abrasion resistant material to protect the ferrite material 37 as well as antenna element 32. It is preferred to additionally provide, either under or within the wear plate 39, a thin conducting wire 40 which substantially fills the antenna opening. The wire 40 is preferably arranged in a loop, with a spacing S between wire segments of about ½ inch, although this dimension can be altered if it is desired to spoil magnetic resonance in a local region of greater or lesser thickness. A small D.C. current is passed thru wire 40 at selected intervals during the measurement cycle, generating local inhomogeneous magnetic fields $B_2$ which extend towards the formation 12 for a distance approximately equal to the spacing S between segments of the wire 40. Within this region of local field inhomogeneity, nuclear magnetic precession is disrupted during part of the measurement cycle, and any resonant conditions which were otherwise created by the intersection of $B_0$ and $B_1$ are substantially altered. The wire 40 constitutes one form of a means for creating localized inhomogeneous fields, and other embodiments are clearly possible. For example, multiple wires, coils, or conductive grids may be used.

Figure 7:
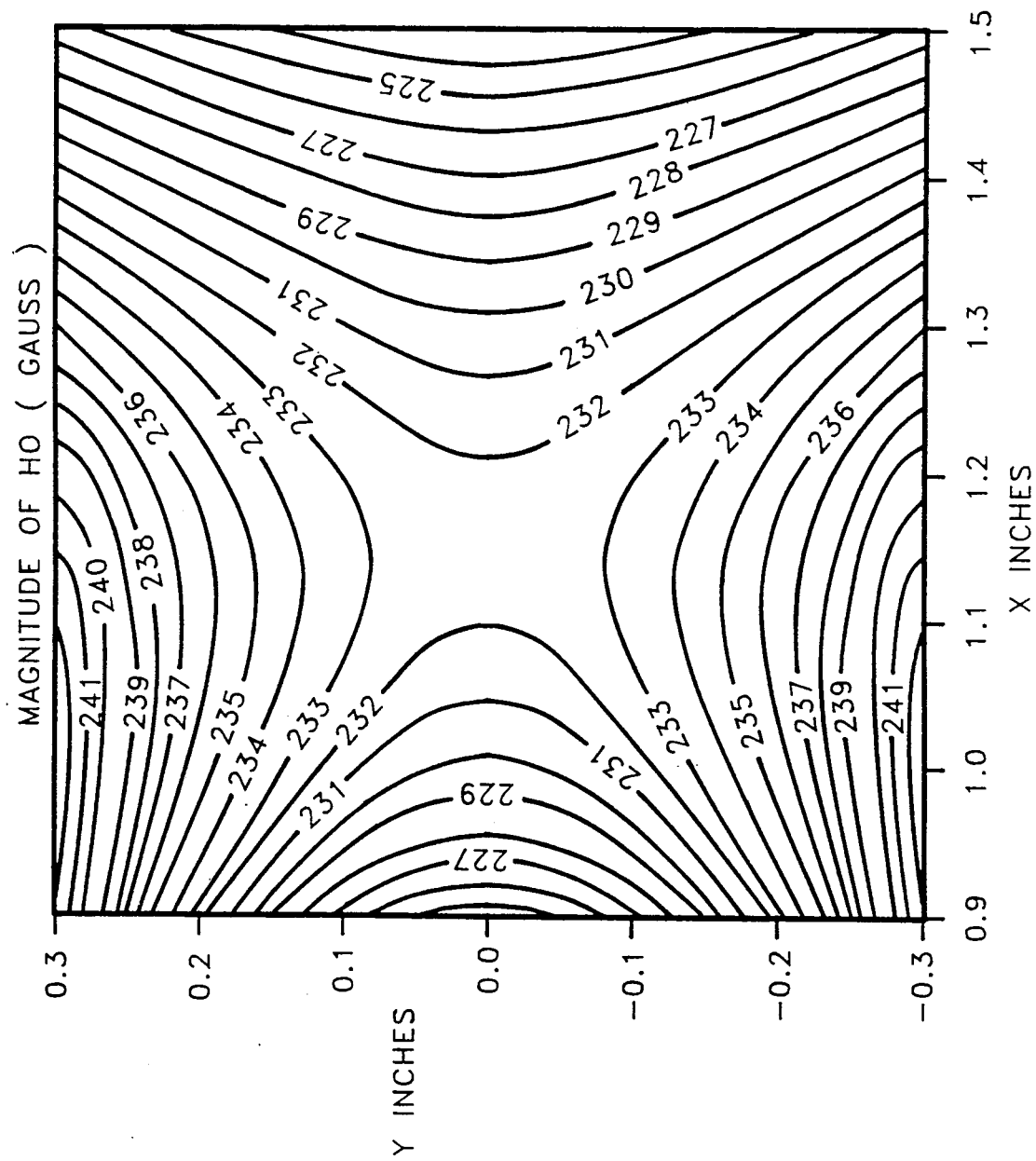
FIG. 7 is a cross-sectional diagram showing magnetic field $B_0$ equal-magnitude lines within the region of investigation shown in FIG. 6.

Spoiling resonance field conditions in the mudcake region is especially advantageous for the preferred embodiment shown in FIGS. 1–8 because typical mudcake contains a high concentration of hydrogen nuclei which may resonate strongly with an applied RF pulse from the antenna 18. The mudcake lying adjacent antenna 18 is subjected to a stronger RF field $B_1$ than even the volume of investigation 9 in formation 12, and therefore may become strongly polarized by $B_1$. Furthermore, there exists high gradient points within ½ inch of the face 14 where the $B_0$ field strength equals the resonant frequency of 232 gauss, as shown in FIGS. 6-7. By imposing the inhomogeneous field $B_2$ within the mudcake region, and spoiling resonance conditions therein, any undesirable NMR contributions from the mudcake are eliminated.

The wire 40 produces a magnetic field $B_2$ having a high spatial gradient $dB_2/dx$, and can alternatively be used to make field gradient type NMR measurements within formation 12. In this case, it would be desirable to arrange the relevant dimensions of wire 40 such that the region of measured NMR resonance overlaps with the gradient field $B_2$.

It is seen that the tool 13 as described measures in a single direction by preferentially directing or "focussing" both the static field $B_0$ and the oscillating field $B_1$, to create the special Volume of Investigation 9. By imposing an additional localized field $B_2$ at regions between the Volume 9 and the tool face 14 which spoils resonance therein, the measurement effectively excludes signals arising from within the mudcake region of the borehole. Furthermore, since the measurement range (distance of sensitivity) of the tool 13 is fairly limited, it is possible to enclose the tool within a reasonably sized calibration cell during testing or calibration of the tool, to exclude magnetic effects of the environment. Consequently, the effective use of the tool 13 for logging oil wells is facilitated.

ELECTRONICS

The electronics requirements for the tool 13 may be mounted in the body 27 or in a separate cartridge or sonde. The preferred circuitry, shown schematically in FIG. 12, operates in three modes: transmitting, damping, and receiving.

In the transmitting mode, the circuit 41 must generate a large power of about 1 kilowatt at a frequency on the order of 1 MHz. for a short precisely timed period, shut off this current very quickly, within about 10 microseconds, and then isolate any signals or noise of the power circuits from coupling with other detection circuitry within the tool 13.

Figure 12:
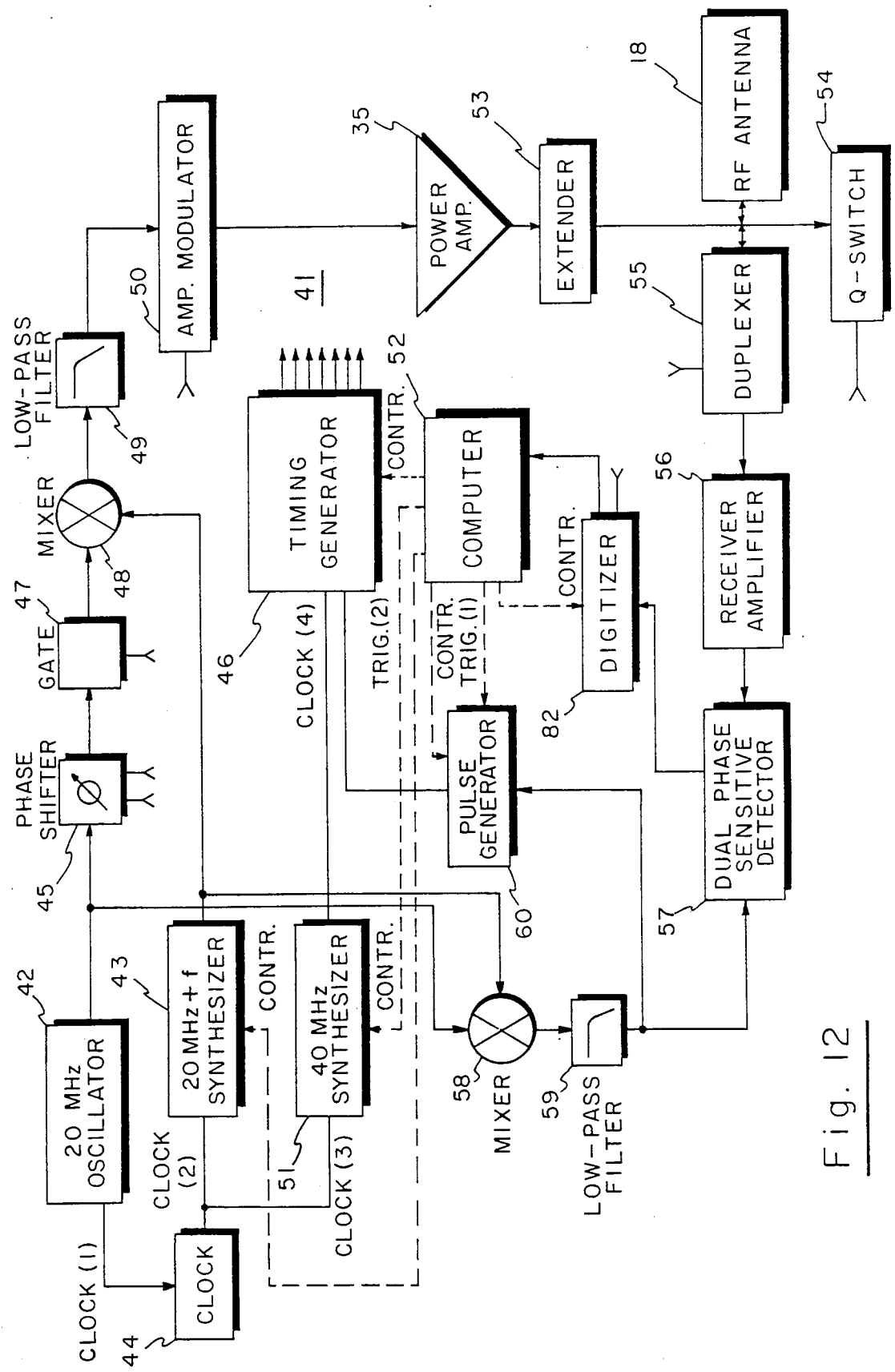
FIG. 12 is a block diagram of circuitry preferably contained in the tool of FIG. 1.

Referring to FIG. 12, the transmitting circuitry comprises a 20 MHz. oscillator 42 and a synthesizer 43 which generates a sinusoidal signal of frequency 20 MHz. $+f$, where $f$ is the desired frequency of operation of the tool. Both oscillators are linked by a clock 44 and kept in synchronization at all times. The output of oscillator 42 is fed to a phase shifter 45, which is controlled by a timing generator 46. The phase shifter 45 can produce shifts of 0, 90, 180, and 270 degrees, as desired by the operator of the tool, and in accordance with the requirements of various measurement schemes such as the Meiboom-Gill sequence. The phase shifted signal passes through a gate 47, and is then combined with the 20 MHz. $+f$ signal from the synthesizer 43 at a mixer 48. The combined signal is fed through a low pass filter 49 which allows only the signal of frequency $f$ to pass. Although the mixer 48 also has other frequency components at its output, these higher frequency $f$ may be turned on and off at any time by appropriate control of the gate 47 by the timing generator 46. Timing generator 46 is kept in precise synchronization with the clock by a 40 MHz synthesizer. Furthermore the oscillators 42, 43, which have much higher frequencies, may be left running at all times without risk that they would adversely affect the detection circuits which operate at the frequency $f$.

The $f$ signal, which retains information of the shifted phase, is passed to the amplitude modulator 50 which adjusts the amplitude to change the signal into a desired pulse shape. Both modulator 50 and gate 47, as well as other components in circuit 41, are controlled by timing generator 46 which is in turn controlled by a computer 52. Referring now to FIGS. 14–15, a typical pulse fashioned by the modulator 50 and gate 47 has a first short time interval t(1) where the amplitude has been increased by the modulator 50, and a second short time interval t(2) during which the amplitude is not increased, and a third short time interval t(3) during which the amplitude is increased and the phase of the signal is reversed. The third period of phase reversal may not be necessary where the shaped pulse is already adequately damped by the Q-switch described hereinbelow. The increased amplitude during t(1) helps to decrease the time it takes to ring up the RF antenna 18, while the reversed-phase signal during t(3) helps to kill the ringing in antenna 18 at the end of the pulse. Therefore, the resultant pulse of magnetic field $B_1$ that is radiated into the formation 12 much more closely resembles a square pulse.

The pulse signal from amplitude modulator 50 is amplified by power amplifier 35 which is capable of out putting approximately 1.2 kilowatts without distorting the signal shape. The signal then passes through an extender 53 which prevents low level noise on the order of ten volts or less from leaking out of amplifier 35 when it is not activated, during the receiving mode. The amplified pulses are then fed to the RF antenna 18, radiating a pulse of magnetic field $B_1$ to resonates nuclear spins in the formation. In between transmitting pulses, the RF antenna 18 receives oscillating magnetic signals of nuclear spin precession.

As previously mentioned, the receiving system of RF probe and matching circuit is designed to have a high Q to maximize the S/N ratio. In such a high Q system, the antenna tends to ring for an undesirably long time, and causes undesirable magnetic spin tipping in the formation. If the antenna is permitted to ring uncontrollably, the transmitted magnetic field pulse bandwith may be substantially reduced. In order to minimize the antenna ringing problem, a Q switch 54 is connected to the line between extender 53 and antenna 18 as a preferred means for damping antenna ringing very quickly at the end of a transmitted pulse. The Q switch 54 closes a circuit at the appropriate time, which changes the impedance of the RF probe system (including RF antenna 18) so that the system is critically damped, and the ringing energy quickly dissipated.

During the receiving mode of operation, Q switch 54 is switched off, and signals from precessing nuclei are received by RF antenna 18 and passed through a duplexer 55 to a receiver amplifier 56. Duplexer 55 protects the receiver amplifier 56 from the high power pulses which pass from extender 53 to the RF antenna 18 during the transmitting and damping modes. During the receiving mode, duplexer 55 is effectively just a 50 ohm cable connecting the antenna 18 to receiver amplifier 56. The detected and amplified signal is then passed to a dual phase sensitive detector 57 which also receives a reference signal that controls the frequency of sensitivity of the detector 57.

The reference signal, also having frequency $f$, is generated by combining the 20 MHz and 20 MHz$+f$ outputs of the oscillator 42 and synthesizer 43 in a second mixer 58, and extracting the lower frequency component $f$ via a low pass filter 59. The output of low pass filter 59, a sinusoidal wave form of frequency $f$, is used as a reference signal for both the detector 57 and a pulse generator 60. The pulse generator 60 generates an appropriate pulse shape in response to control and triggering signals from the computer 52, and triggers the timing generator 46.

The detector 57, in response to the reference signal and the formation NMR signal from receiver amplifier 56, obtains a measured NMR resonance signal of frequency $f$ from the desired volume of investigation, and passes it to the digitizer 82. The digitized signal is then forwarded to the computer 52 for processing and/or formatting as desired by the operator.

Q-SWITCH

Figure 16:
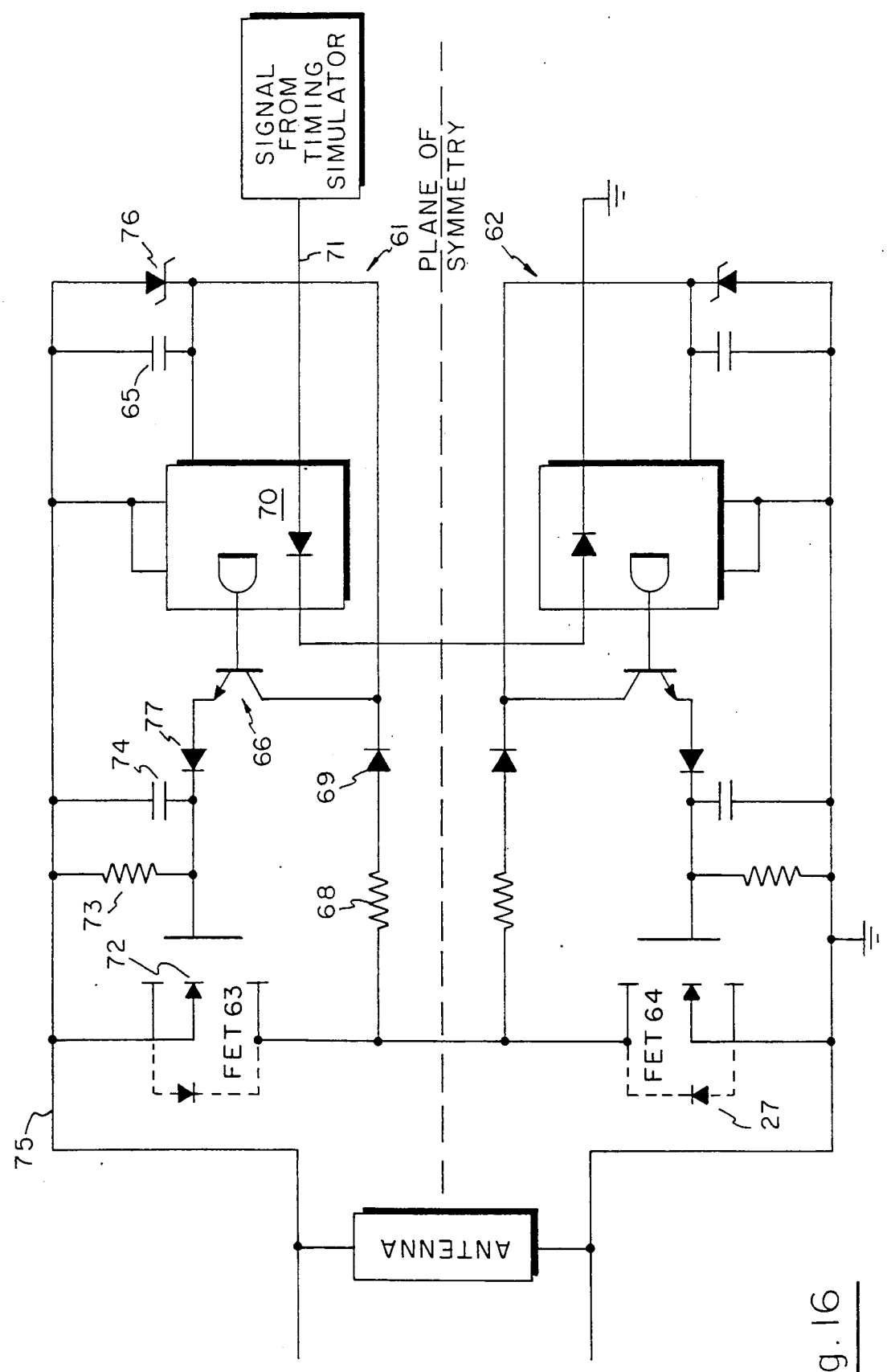
FIG. 16 is a circuit diagram of a Q switch in accordance with the present invention.

Referring to FIG. 16, the Q Switch 54 comprises two symmetric circuits 61 and 62, shown on the top and bottom, respectively of the figure. The purpose of the Q switch 54 is to introduce a resistive element into the antenna network, in parallel with the capacitors 38 (see FIG. 9), so as to critically damp the network, in accordance with the formula $R_C = \frac{1}{2}(L/C)^{\frac{1}{2}}$. For example, where $L = 1.1 \times 10^{-7}$ H., $C = 2.3 \times 10^{-7}$ F. and assuming an operating frequency of 1 MHz, the needed additional resistance to critically damp antenna 18 would be $R_C = 0.36$ ohm.

Q switch 54 utilizes two field effect transistors (FET's) 63, 64 connected back to back, to provide approximately the resistance of 0.36 ohms, when they are closed. Two FET's are needed since each one is effective in developing a resistance to a high voltage therein of only one polarity due to an effective internal diode 67, and the ringing of the antenna 18 is a bipolar oscillating voltage. If the resistive value needed for critically damping an antenna 18 is greater than the resistance of the FET's 63,64, additional resistive elements may be inserted in series.

When the FET's 63, 64 are switched open, the circuit is an open circuit and has no effect on the antenna network. Thus, Q switch 54 is open during the transmitting mode and during the receiving mode of the circuitry (FIG. 12), and closed during the damping mode which is shown in FIGS. 14-15 as the time period t(3).

The remaining circuitry in FIG. 16 comprise means for gating the FET's 63, 64 on and off with minimum noise being introduced into the antenna network. Since the circuits 61,62 are essentially identical, only one of them will be described below.

In the transmitting mode, during the RF pulse, a 20 nF capacitor 65 and the collector of an intermediate stage transistor 66 are charged through the line comprising diode 67, resistor 68 (51 ohms) and diode 69, where diode 67 is part of the FET 64 of the lower symmetric circuit 62. The base of transistor 66 is connected to an optical coupler 70 which is controlled by a signal on line 71 from the timing generator 46. The optical coupler 70 is preferably used with the NMR logging tool because it ensures isolation between the switching signals and the high voltage on the antenna.

The emitter of intermediate stage transistor 66 is connected via diode 77 to the gate 72 of the FET 63. The gate 72 is also connected to a 1 k resistor 73 and a 8.2 nF capacitor 74, which are in turn connected to the source line 75, to constitute a R-C combination high pass filter between gate 72 and source line 75. This R-C filter ensures that the source-to-gate voltage never reaches excessive levels during the transmission of an RF pulse and also provides a self-turnoff time constant. A zener diode 76 connected in parallel with the 20 nF capacitor 65 to prevent excessively large voltages from damaging the optical coupler 70.

During the damping mode, a signal from the timing generator 46 is passed via line 71, to activate the optical coupler 70 and charge the base of the intermediate stage transistor 66. The transistor 66 is turned on, causing a voltage to be applied to gate 72, making the FET 63 conductive, and providing damping of the antenna network.

During operation of the tool 13, the operator enters into the computer 52 information respecting the type of measurement sequence to be taken. Computer 52 then sets the sequence of electronic steps needed for the equipment to implement the measurement sequence. The computer 52 controls the timing generator 46 which in turn sends control signals to the various components of circuit 41 to control the polarizing pulse height, length, frequency, relative phases of sequential pulses, receiving mode period and frequency, and the timing of all of the above.

Because the high Q antenna 18 can be rapidly damped after transmitting a 1 kilowatt RF pulse, the tool 13 is capable of resonating a targeted formation 12 with many successive pulses in a short time. The deadtime between a transmitted pulse and the commencing of the receiving mode, about 25 microseconds, is about 1000 times shorter than the deadtime of the previous commercially available logging tool. Using peak power of 100 W, the pulses can have a duration of about 40 μsec. and it is possible to have as many as 1000 pulses within a measurement cycle lasting 1 second.

In addition to the NMR measurements heretofore known to be performed by the existing commercial logging tool discussed in the previously cited references, a Carr-Purcell type measurement may also be made to measure the transverse relaxation time $T_2$. This sequence is also commonly known as a 180°-90° sequence, where the angles refer to the degree of tipping undertaken by the precessing protons during the measurement process. Other measurement sequences which can be undertaken with the present apparatus include the Meiboom-Gill sequence, as described in the cited Ferrar and Becker textbook, or a 90°-τ-90° sequence of the type described in G. G. McDonald and J. S. Leigh, Jr., "A New Method for Measuring Longitudinal Relaxation," *Journal of Magnetic Resonance*, Vo. 9, pp. 358-362 (1973), which measures the longitudinal relaxation time $T_1$. It is contemplated that additional types of borehole NMR measurements may be devised in accordance with the invention to advantageously investigate the magnetic properties of earth formations.

PREPOLARIZATION

When the tool 13 is used to make continuous logs, without stopping the tool for each measurement, an alternative embodiment may be preferred, to further improve the S/N beyond what has already been discussed. Referring to FIG. 1, a prepolarizing magnet 19 is installed within the tool 13 above the position of the main magnet array 17, to magnetically polarize the formation 11 before the magnet array 17 has reached proximity to it for measurement. The field of the prepolarizing magnet 19 should be similar to that of the magnet array 17 in orientation, but preferably much stronger, so as to polarize a much larger population of nucleii. As the tool is moved up the borehole, magnet array 17 comes into proximity of formation 11, and radiates it with RF pulses. However, because of the prepolarization, a larger number of nuclei are aligned with the field $B_0$ of the magnet array 17 within the volume of substantially homogeneous filed, and a correspondingly larger signal is produced.

Figure 17:
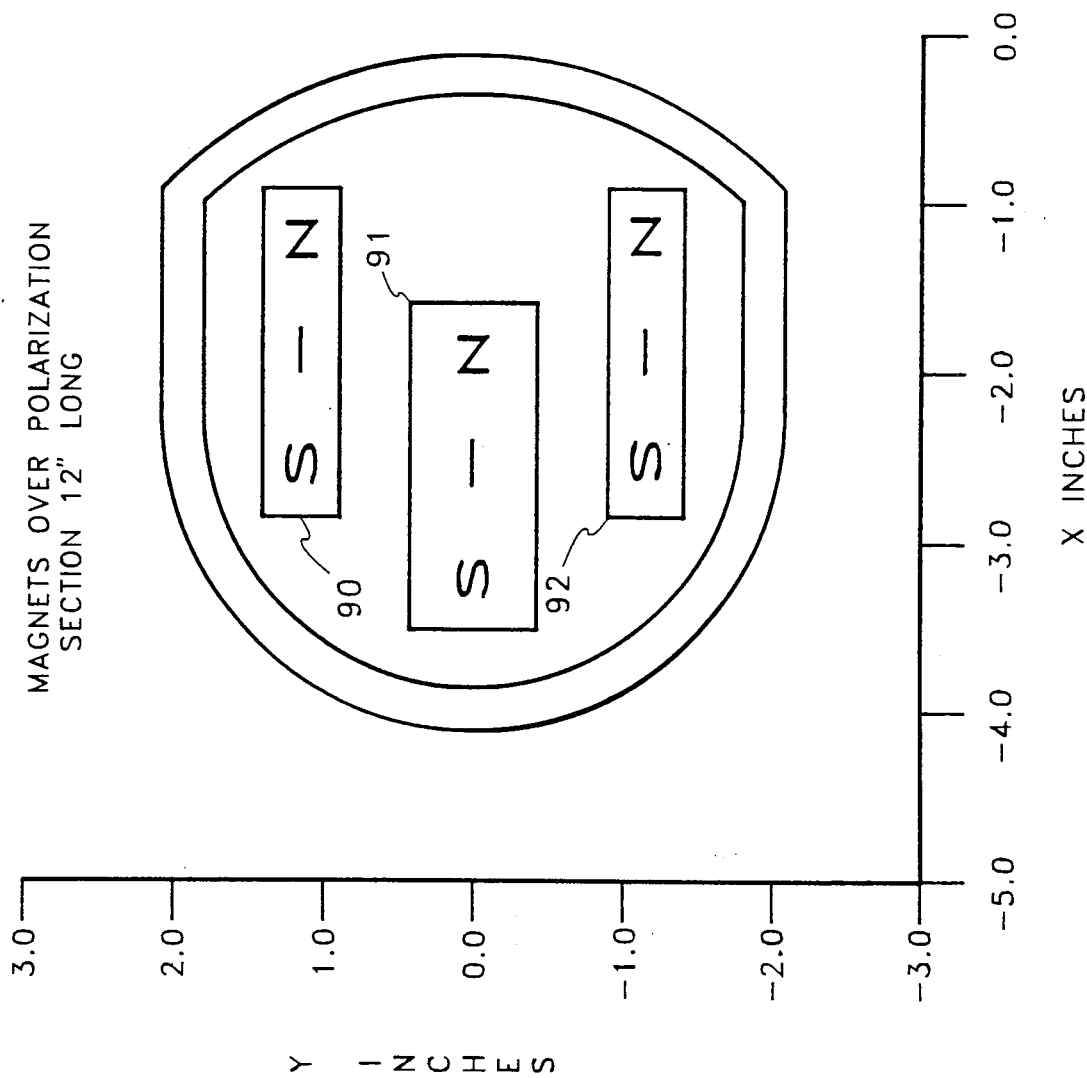
FIG. 17 is an enlarged cross-sectional plan view of a prepolarizing magnet which includes three slab magnets, in accordance with an alternative embodiment of the invention.
Figure 18:
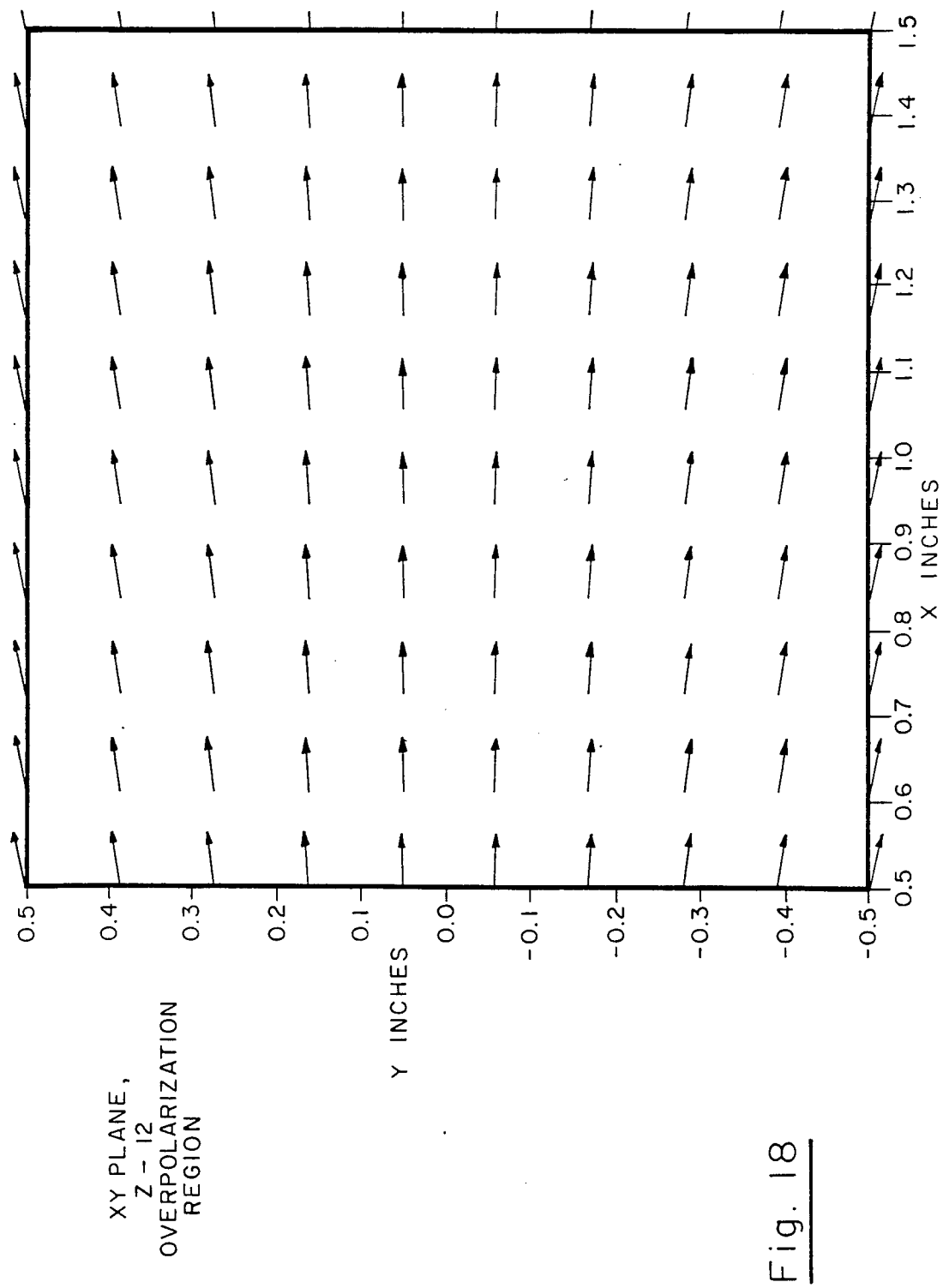
FIG. 18 is a diagram showing the magnetic field lines, represented by short arrows, within a region of investigation in front of the prepolarizing magnet of FIG. 17.
Figure 19:
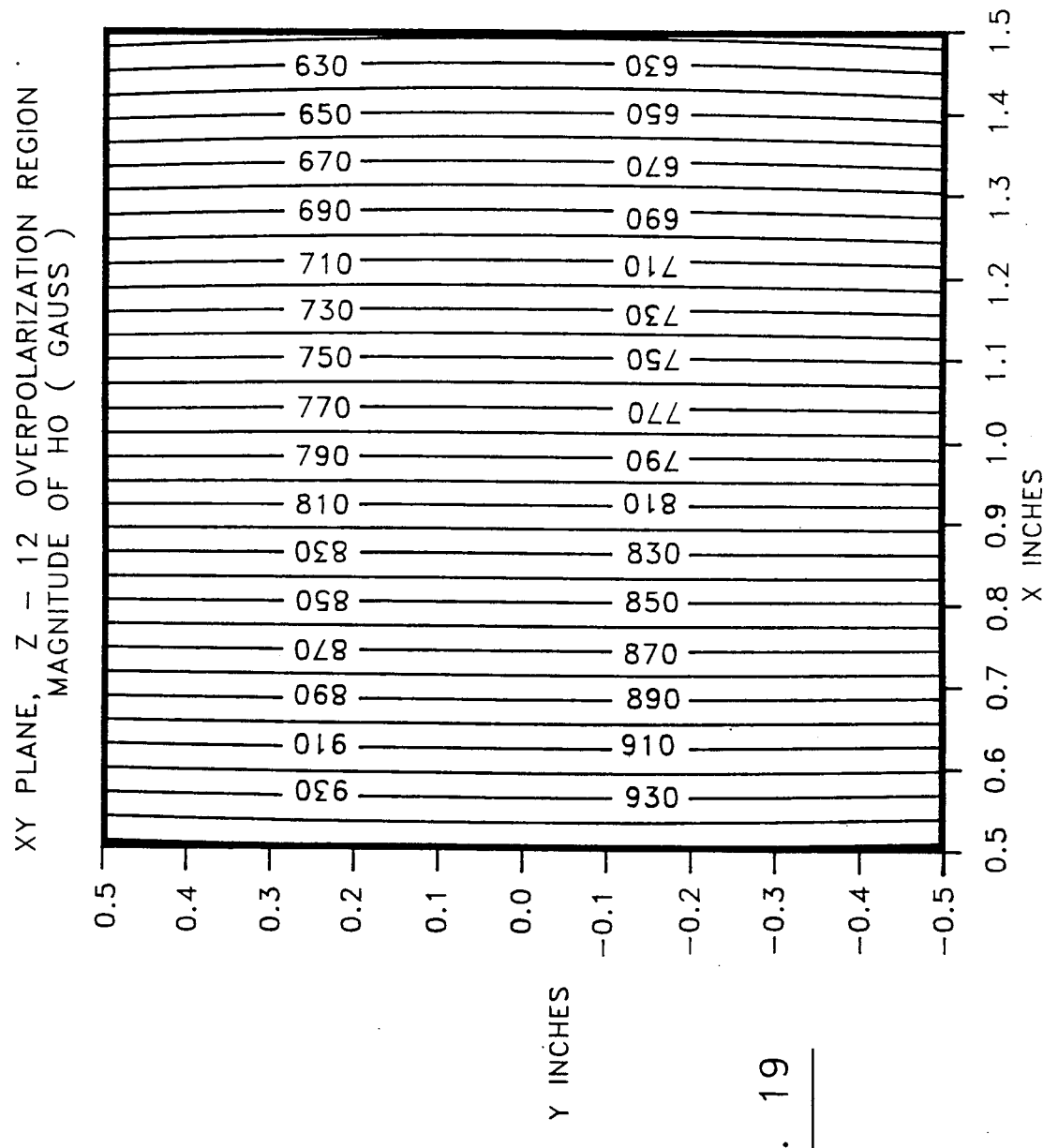
FIG. 19 is a diagram showing magnetic equal-magnitude lines within the region of investigation of FIG. 17.

The prepolarization magnet is preferably an array magnets in a configuration such as that shown in FIG. 17, comprising magnets 90, 91 92, aligned with similar poles facing in the same direction to maximize the field strength that is produced in the formation. Obviously, other combinations of magnets can produce a similar field, and a single magnet may be used instead of an array as shown. Referring to FIGS. 18-19, the magnetic field $B_P$ of the prepolarizing magnet 19 can be substantially less homogeneous than the field of the magnet array 17, without adversely affecting the bandwith or S/N of the NMR measurement which depends only on the existing static field $B_0$ at the time of the measurement.

The preferred embodiments may obviously be modified in various ways without departing from the spirit of the invention, as would be clear to persons skilled in the art. For example, the prepolarization magnet need not be constructed of the configuration of magnets as shown in FIG. 17, but may be a single magnet or some other arrangement. Slab magnets have been used because the slim profile tends to minimize demagnetization effects, and they are relatively easy to assemble. Since they are large and have very high energy density, the ease the handling and assembly of the magnets are significant considerations, and the simple configuration discussed herein has been found to be advantageous from many standpoints. Nevertheless, other types of magnets may be used, in accordance with the invention.

If stationary measurements are desired, there is the possibility that differential sticking and other dynamic borehole effects would cause the tool 13 to become stuck. Thus, if such stationary measurements are to be made, it is preferable to provide means for prying tool face 14 away from the borehole wall after the completion of a measurement cycle at depth. For example, two push-off pistons 93, 94, shown in FIG. 1 in dotted lines, may be hydraulically actuated to force the tool 13 away from the borehole wall after the arm 15 has been retracted.

It has been described and illustrated herein novel apparatus and methods for measuring and interpreting magnetic characteristics of formations traversed by a borehole. Those skilled in the art will recognize that numerous variations and modifications may be made without departing from the scope of the present invention. Accordingly, it should be clearly understood that the forms of the invention described hereinabove are exemplary, and are not intended as limitations on the scope of the present invention, which should be defined only by the claims appended hereto.

We claim:

1. An apparatus for investigating a characteristic of earth formations traversed by a borehole, comprising a body adapted for longitudinal movement in the borehole, said body comprising:
   first means for producing a static and substantially homogeneous magnetic field in volume of said formation directed to one side of the body, said volume being elongated in the longitudinal direction of the borehole axis and having a substantial cross-sectional extent in a plane perpendicular to the direction of thhe borehole axis; and
   second means for radiating said volume of formation with oscillating magnetic fields and for detecting a signal representative of nuclear magnetic precession of a population of particles in said formation.

2. An apparatus as in claim 1 wherein said second means includes an antenna mounted on said one side of the first means.

3. An apparatus as in claim 1 wherein said body further comprises a substantially nonmagnetic metallic support, and said second means further includes antenna means mounted on said one side of the body externally of said support, whereby said antenna means is electromagnetically shielded by the metallic support.

4. An apparatus as in claim 3 wherein said support comprises a metallic sheath on said body.

5. An apparatus as in claim 3 wherein said antenna means is operable to produce oscillating magnetic fields in said formation.

6. An apparatus as in claim 3 wherein said antenna means is operable to detect a signal representative of nuclear magnetic precession in said formation.

7. An apparatus as in claim 3 wherein said antenna means is operable both to produce oscillating magnetic fields and to detect signals representative of nuclear magnetic precession in said formation.

8. An apparatus as in claim 1 wherein said static and substantially homogeneous magnetic field projects substantially radially out of said one side of the body, through said volume.

9. An apparatus as in claim 1 wherein the spatial derivative of the field within said volume is approximately zero.

10. An apparatus as in claim 1 further comprising means for applying said one side of the body against the wall of said borehole.

11. An apparatus as in claim 3 further comprising means for applying said one side of the body against the wall of said borehole.

12. An apparatus as in claim 11 wherein said apparatus comprises a logging tool suspended from a wireline.

13. An apparatus as in claim 1 wherein said first means comprises a plurality of permanent magnets affixed in said body in a predetermined configuration.

14. An apparatus as in claim 1, wherein said volume is spaced from said body.

15. An apparatus as in claim 1 wherein said volume is spaced from said body by more than the expected thickness of mudcake on the borehole wall.

16. An apparatus as in claim 11 wherein said volume is spaced from said body by at least approximately ½ inch.

17. An apparatus as in claim 1, wherein said first means comprises:
a first magnet having a magnetic pole pointed generally in the direction of said volume;
a second magnet having a similar magnetic pole pointed generally in the direction of said volume; and
a third magnet, positioned between the first and second magnets, having an opposite magnetic pole pointed generally in the direction of said volume.

18. An apparatus as in claim 17 wherein said first, second and third magnets are bar magnets.

19. An apparatus as in claim 18 wherein said bar magnets are permanent bar magnets.

20. An apparatus as in claim 18 wherein said first, second and third magnets are substantially elongated in a direction parallel to the borehole.

21. An apparatus as in claim 20 wherein said first, second and third magnets are parallel to each other along their axes of elongation.

22. An apparatus as in claim 21 wherein said magnets are permanent bar magnets.

23. An apparatus as in claim 1 further comprising third means for producing a static magnetic field oriented parallel to said homogeneous magnetic field and offset therefrom, and having at least the same intensity as said homogeneous magnetic field.

24. An apparatus as in claim 23 wherein said static magnetic field produced by said third means is positioned longitudinally above said volume of homogeneous magnetic field.

25. An apparatus as in claim 24 wherein said third means includes at least one magnet positioned within said body above said first means.

26. An apparatus as in claim 3 wherein said antenna means comprises a conductive depression on said one side of the body and facing the formation wall, and a conductive element in said depression.

27. An apparatus as in claim 26 wherein said conductive depression is a substantially semicylindrical cavity and the conductive element comprises a conductive rod positioned coaxially in the simicylindrical cavity.

28. An apparatus as in claim 27 wherein said cavity and conductive, element are substantially elongated, parallel to each other, and parallel to the borehole axis.

29. An apparatus as in claim 28 wherein said cavity and conductive element are approximately the same length as the longitudinal dimension of said volume.

30. An apparatus as in claim 28 wherein the space between the conductive depression and the conductive element is substantially filled with a nonconductive material having high magnetic permeability.

31. An apparatus as in claim 27 wherein the diameter of said rod is substantially less than the width of the semicylindrical cavity.

32. A method for investigating a magnetic characteristic of a population of particles in an earth formation traversed by a borehole, comprising:
producing a static magnetic field having radially directed field lines and being substantially homogeneous in a volume of said formation on one side of the apparatus, said volume being elongated in the longitudinal direction of the borehole axis and having a substantial cross-sectional extent in the plane perpendicular to the direction of the borehole axis;
radiating said volume of formation with oscillating magnetic fields; and
detecting NMR signals at the Larmor frequency of said particles under the influence of said static and substantially homogeneous magnetic field within said volume.

33. A method as in claim 32, wherein said step of radiating said volume includes using a RF antenna to radiated focused oscillating fields in the direction of said volume.

34. A method as in claim 33 wherein said step of producing said static and substantially homogeneous magnetic field further comprises focussing the static fields of a plurality of magnets within said apparatus, such that said volume is spaced from said apparatus by at least the expected distance between the apparatus and the formation to be measured.

35. A method as in claim 34 wherein said static and substantially homogeneous magnetic field in said volume has radially directed field lines, and said oscillating magnetic fields are perpendicular thereto.

36. An apparatus as in claim 3, wherein said first means comprises a plurality of permanent magnets affixed in said body in a predetermined configuration.

37. An apparatus as in claim 2, wherein said volume is spaced from said body.

38. An apparatus as in claim 3, wherein said first means comprises:
a first magnet having a magnetic pole pointed generally in the direction of said volume;
a second magnet having a similar magnetic pole pointed generally in the direction of said volume; and
a third magnet, positioned between the first and second magnets, having ann opposite magnetic pole pointed generally in the direction of said volume.

39. An apparatus as in claim 11, wherein said antenna means comprises a conductive depression on said one side of the body and facing the formation wall, and a conductive element in said depression.

40. A apparatus for investigating a characteristic of eart formations traversed by a borehole, comprising a body adapted for longitudinal movement in the borehole, said body comprising:

first means for producing a static and substantially homogeneous magnetic field in a substantial volume of said formation directed to one side of the body, said first means comprising a first magnet having a magnetic pole pointed generally in the direction of said volume, a second magnet having a similar magnetic pole pointed generally in the direction of said volume, and a third magnet, positioned between the first and second magents, having an opposite magnetic pole pointed generally in the direction of said volume; and second means for radiating said volume of formation with oscillating magnetic fields and for detecting a signals representative of nuclear magnetic precession of a population of particles in said formation.

41. An apparatus as in claim 40 wherein said first, second and third magnets are bar magnets.

42. An apparatus as in claim 41 wherein said bar magnets are permanent bar magnets.

43. An apparatus as in claim 41 wherein said first, second and third magnets are substantially elongated in a direction parallel to the borehole axis.

44. An apparatus as in claim 43 wherein said first, second and third magnets are parallel to each other along their axes of elongation.

45. An apparatus as in claim 42 wherein said magnets are permanent bar magnets.

46. An apparatus for investigating a characteristic of earth formations traversed by a borehole, comprising a body adapted for longitudinal movement in the borehole, said body comprising:

a substantially nonmagnetic metallic support which contains a first means for producing a static and substantially homogeneous magnetic field in a volume of said formation directed to one side of the body; and second means, including an antenna mounted externally of said support, for radiating said volume of formation with oscillating magnetic fields and for detecting a signal representative on nuclear magnetic precession of a population of particles in said formation, said antenna being electromagnetically shielded by said support.

47. An apparatus as in claim 46 wherein said antenna is adjacent said support and located on said one side of the body.

48. An apparatus as in claim 46, further comprising means for applying said one side of the body against the wall of said borehole.

49. An apparatus as in claim 47, further comprising means for applying said one side of the body against the wall of said borehole.

50. An apparatus as in claim 47 wherein said antenna means comprises a conductive depression in said support, and a conductive element in said depression.

51. An apparatus as in claim 50 wherein said conductive depression is a substantially semicylindrical cavity and said conductive element comprises a conductive rod positioned coaxially in the semicylindrical cavity.

52. An apparatus as in claim 51 wherein said cavity and conductive element are substantially elongated, parallel to each other, and parallel to the borehole axis.

53. An apparatus as in claim 51 wherein the space between the conductive depression and the conductive element is substantially filled with a nonconductive material having high magnetic permeability.

54. An apparatus as in claim 51 wherein the diameter of said rod is substantially less than the width of the semicylindrical cavity.

55. An apparatus as in claim 1 wherein said first means comprises a plurality of magnets having like magnetic poles pointed generally in the direction of said volume.

56. An apparatus as in claim 55 wherein each of said plurality of magnets is a bar magnet.

57. An apparatus as in claim 56 wherein said bar magnets are permanent bar magnets.

58. An apparatus as in claim 56 wherein said magnets are substantially elongated in a direction parallel to the borehole axis.

59. An apparatus as in claim 58 wherein said magnets are parallel to each other along their axes of elongation.

60. An apparatus as in claim 59 wherein said magnets are permanent bar magnets.

* * * * *